(12) United States Patent
Clark et al.

(10) Patent No.: US 9,416,414 B2
(45) Date of Patent: Aug. 16, 2016

(54) DELAYING REAL-TIME SEQUENCING

(71) Applicant: Pacific Biosciences of California, Inc., Menlo Park, CA (US)

(72) Inventors: Tyson A. Clark, Menlo Park, CA (US); Jonas Korlach, Newark, CA (US); Cheryl Heiner, La Honda, CA (US); Kevin Travers, Menlo Park, CA (US); Erik Miller, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 14/521,109

(22) Filed: Oct. 22, 2014

(65) Prior Publication Data

US 2015/0118685 A1 Apr. 30, 2015

Related U.S. Application Data

(60) Provisional application No. 61/895,337, filed on Oct. 24, 2013.

(51) Int. Cl.
*C12Q 1/68* (2006.01)
(52) U.S. Cl.
CPC .................................. *C12Q 1/6869* (2013.01)
(58) Field of Classification Search
None
See application file for complete search history.

(56) References Cited

U.S. PATENT DOCUMENTS

| | | | |
|---|---|---|---|
| 5,547,839 | A | 8/1996 | Dower et al. |
| 6,210,896 | B1 | 4/2001 | Chan |
| 6,255,083 | B1 | 7/2001 | Williams |
| 6,787,308 | B2 | 9/2004 | Balasubramanian et al. |
| 7,056,661 | B2 | 6/2006 | Korlach et al. |
| 7,279,337 | B2 * | 10/2007 | Zhu ................... C12Q 1/6825 422/50 |
| 7,315,019 | B2 | 1/2008 | Turner et al. |
| 8,003,330 | B2 | 8/2011 | Heiner et al. |
| 8,133,672 | B2 | 3/2012 | Bjornson et al. |
| 8,153,375 | B2 | 4/2012 | Travers et al. |
| 8,236,499 | B2 | 8/2012 | Patel et al. |
| 8,247,216 | B2 | 8/2012 | Zaccarin et al. |
| 8,252,911 | B2 | 8/2012 | Bjornson et al. |
| 8,304,191 | B2 | 11/2012 | Eid et al. |
| 8,658,365 | B2 | 2/2014 | Bjornson et al. |
| 2003/0096253 | A1 | 5/2003 | Nelson |
| 2003/0190647 | A1 | 10/2003 | Odera |
| 2003/0215862 | A1 | 11/2003 | Parce et al. |
| 2004/0048300 | A1 | 3/2004 | Sood et al. |
| 2004/0152119 | A1 | 8/2004 | Sood et al. |
| 2004/0224319 | A1 | 11/2004 | Sood et al. |
| 2009/0118129 | A1 | 5/2009 | Turner |
| 2011/0183320 | A1 | 7/2011 | Flusberg et al. |
| 2012/0009567 | A1 | 1/2012 | Fedorov et al. |
| 2012/0071359 | A1 | 3/2012 | Sun et al. |
| 2012/0196279 | A1 | 8/2012 | Underwood et al. |
| 2012/0322666 | A1 | 12/2012 | Pham et al. |
| 2012/0322692 | A1 | 12/2012 | Pham et al. |
| 2014/0017674 | A1 | 1/2014 | Fedorov et al. |
| 2014/0134610 | A1 | 5/2014 | Pham et al. |
| 2014/0134629 | A1 | 5/2014 | Turner et al. |
| 2014/0179564 | A1 | 6/2014 | Korlach et al. |
| 2014/0206550 | A1 | 7/2014 | Bjornson et al. |

FOREIGN PATENT DOCUMENTS

| | | |
|---|---|---|
| WO | 9106678 A1 | 5/1991 |
| WO | 9627025 A1 | 9/1996 |
| WO | 9905315 A2 | 2/1999 |

OTHER PUBLICATIONS

Parameswaran et al., "A pyrosequencing-tailored nucleotide barcode design unveils opportunities for large-scale sample multiplexing," Nucleic Acids Research, 2007, vol. 35, No. 19, e130, pp. 1-9.*
Eid et al., "Real-Time DNA Sequencing From Single Polymerase Molecules," Science (2009) 323:133-138.
Flusberg et al., "Direct Detection of DNA Methylation During Single- Molecule, Real-Time Sequencing," Nature Methods (2010) 7:461-465.
Korlach et al., "Selective Aluminum Passivation for Targeted Immobilization of Single DNA Polymerase Molecules in Zero-Mode Waveguide Nanostructures," PNAS (2008) 105(4).1176-1181.
Levene et al., "Zero-mode Waveguides for Single-molecule Analysis at High Concentration" Science (2003) 299:682-686.
Pastor-Palacios et al., "A Transposon-Derived DNA Polymerase from Entamoeba Histolytica Displays Intrinsic Strand Displacement, Processivity and Lesion Bypass," PLOS One (2012) 7(11):e49964.
Travers et al., "A Flexible and Efficient Template Format for Circular Consensus Sequencing and SNP Detection," Nucleic Acids Research (2010) 38:e159.

* cited by examiner

*Primary Examiner* — Young J Kim
(74) *Attorney, Agent, or Firm* — Deana A. Arnold; David C. Scherer

(57) ABSTRACT

Methods, compositions, and systems are provided that allow for reliable sequencing of the initial sequence region of a sequence of interest. The methods of the invention allow for more reliable barcoding of subpopulations of nucleic acids to be sequenced.

26 Claims, 11 Drawing Sheets

DELAYING REAL-TIME SEQUENCING

CROSS-REFERENCE TO RELATED APPLICATIONS

This application claims the benefit of U.S. Provisional Application No. 61/895,337, filed Oct. 24, 2013, the full disclosure of which is incorporated herein by reference in its entirety for all purposes.

STATEMENT REGARDING FEDERALLY SPONSORED RESEARCH

Not Applicable.

BACKGROUND OF THE INVENTION

Nucleic acid sequences encode the necessary information for living things to function and reproduce, and are essentially a blueprint for life. Determining such sequences is therefore a tool useful in pure research into how and where organisms live, as well as in applied sciences such drug development. In medicine, sequencing tools can be used for diagnosis and to develop treatments for a variety of pathologies, including cancer, heart disease, autoimmune disorders, multiple sclerosis, or obesity. In industry, sequencing can be used to design improved enzymatic processes or synthetic organisms. In biology, such tools can be used to study the health of ecosystems, for example, and thus have a broad range of utility.

An individual's unique DNA sequence provides valuable information concerning their susceptibility to certain diseases. The sequence will provide patients with the opportunity to screen for early detection and to receive preventative treatment. Furthermore, given a patient's individual genetic blueprint, clinicians will be capable of administering personalized therapy to maximize drug efficacy and to minimize the risk of an adverse drug response. Similarly, determining the blueprint of pathogenic organisms can lead to new treatments for infectious diseases and more robust pathogen surveillance. Whole genome DNA sequencing will provide the foundation for modern medicine. Sequencing of a diploid human genome requires determining the sequential order of approximately 6 billion nucleotides. Sequencing of RNA can also provide valuable information relating to which portions of the genome are being expressed by single cells or groups of cells. Greater knowledge of expression can provide keys to understanding and treating many diseases and conditions, including providing a molecular level understanding of the progression of cancer.

A variety of methods have been developed with the goal of providing efficient, cost effective, accurate, and high throughput sequencing. Single-molecule nucleic acid sequencing-by-synthesis is a sequencing method that has the potential to revolutionize the understanding of biological structure and function. When simultaneously performing sequencing on thousands of molecules, in some cases, it has proven difficult to initiate sequencing to reliably read the first set of bases a sequence. The instant invention provides improved sequencing methods and compositions for reliably sequencing the initial bases in a sequence of interest.

BRIEF SUMMARY OF THE INVENTION

In certain aspects of the invention, methods for delaying the sequencing of a sequence of interest in a single-molecule, real-time sequencing reaction are provided that comprises simultaneously initiating a plurality of single-molecule, real-time sequencing reactions on a plurality of polymerase-template complexes, wherein each of the polymerase-template complexes comprises a polymerase enzyme and a nucleic acid template wherein the nucleic acid template comprises, in order, a priming region, a runway region, and an insert region comprising a sequence of interest, wherein the time from the initiation of the sequencing reactions to the time of sequencing the insert region is greater than about 30 seconds for a majority of the polymerase-template complexes. In some embodiments, portions of the nucleic acid templates are identical, e.g., the priming regions and/or the runway regions may be the same or substantially the same across all the nucleic acid templates in the polymerase-template complexes. The nucleic acid template preferably comprises a double-stranded region with a hairpin adaptor connecting the strands at an end of the double-stranded region. Optionally, the nucleic acid template comprises two hairpin adaptors, one at each end of the double-stranded region. During the sequencing reactions, the incorporation of nucleotide residues is detected, e.g., optically, electronically or magnetically, and this detection can be accomplished using fluorescence, electrochemistry, capacitance, conductivity, impedance, or a field effect transducer (FET). The runway region is optionally at least 200 nucleotides, and is sometimes greater than 500 nucleotides, and in specific embodiments is between 200 and 2000 nucleotides. In certain embodiments, the runway region comprises one or more modified bases that are absent from the insert region. Preferably, the time from the initiation of the sequencing reactions to the time of sequencing the insert region is greater than about 60 seconds for a majority of the polymerase-template complexes. Optionally, the nucleic acid templates comprise a barcode region between the runway region and the insert region.

In other aspects of the invention, methods for delaying the sequencing of a sequence of interest in a single-molecule, real-time sequencing reaction are provided that comprises simultaneously performing a plurality of single-molecule, real-time sequencing reactions on a plurality of template complexes, wherein each of the template complexes comprises a nucleic acid template that comprises, in order, a priming region, a runway region, and an insert region comprising a sequence of interest, wherein the runway region comprises at least 200 nucleotides. In some embodiments, portions of the nucleic acid templates are identical, e.g., the priming regions and/or the runway regions may be the same or substantially the same across all the nucleic acid templates in the polymerase-template complexes. The nucleic acid template preferably comprises a double-stranded region with a hairpin adaptor connecting the strands at an end of the double-stranded region. Optionally, the nucleic acid template comprises two hairpin adaptors, one at each end of the double-stranded region. During the sequencing reactions, the incorporation of nucleotide residues is detected, e.g., optically, electronically or magnetically, and this detection can be accomplished using fluorescence, electrochemistry, capacitance, conductivity, impedance, or a field effect transducer (FET). In certain preferred embodiments, the single-molecule, real-time sequencing reaction comprises observing labels corresponding to labeled nucleotides during polymerase mediated nucleic acid synthesis. In other preferred embodiments, the single-molecule, real-time sequencing reaction comprises nanopore sequencing. The runway region is optionally greater than 500 nucleotides, and in specific embodiments is between 200 and 2000 nucleotides. In certain embodiments, the runway region comprises one or more modified bases that are absent from the insert region. Preferably, the time from the initiation of the sequencing reactions to the time of sequencing the insert region is greater than about 30, 40, 50, or 60 seconds for a majority of the polymerase-template complexes. Optionally, the nucleic acid templates comprise a barcode region between the runway region and the insert region.

In further aspects of the invention, methods for real-time single-molecule sequencing of a nucleic acid are provided that comprises providing, on a substrate, a plurality of individually resolvable polymerase-template complexes, each comprising a polymerase enzyme and a nucleic acid template having, in this order: a priming region, a runway region, and an insert region comprising a sequence of interest, exposing the substrate to a sequencing reaction mixture comprising labeled nucleotides comprising phospholinked labels such that sequencing reactions by the polymerase-template complexes proceed, and observing a time sequence of signals from the labels corresponding to the incorporation of the nucleotide residues of the labeled nucleotides to provide sequence reads comprising sequence data for both the runway region and the insert region, wherein 80% or more of the sequence reads include the first 10 nucleotides of the insert region. In some embodiments, portions of the nucleic acid templates are identical, e.g., the priming regions and/or the runway regions may be the same or substantially the same across all the nucleic acid templates in the polymerase-template complexes. The nucleic acid template preferably comprises a double-stranded region with a hairpin adaptor connecting the strands at an end of the double-stranded region. Optionally, the nucleic acid template comprises two hairpin adaptors, one at each end of the double-stranded region. During the sequencing reactions, the incorporation of nucleotide residues is detected, e.g., optically, electronically or magnetically, and this detection can be accomplished using fluorescence, electrochemistry, capacitance, conductivity, impedance, or a field effect transducer (FET). The runway region is optionally at least 200 nucleotides, and is sometimes greater than 500 nucleotides, and in specific embodiments is between 200 and 2000 nucleotides. In certain embodiments, the runway region comprises one or more modified bases that are absent from the insert region. Preferably, the time from the initiation of the sequencing reactions to the time of sequencing the insert region is greater than about 30, 40, 50, or 60 seconds for a majority of the polymerase-template complexes. Optionally, the nucleic acid templates comprise a barcode region between the runway region and the insert region.

In another aspect of the invention, methods for real-time single-molecule sequencing of a nucleic acid are provided that comprises providing, on a substrate, a plurality of individually resolvable polymerase-template complexes, each comprising a polymerase enzyme and a nucleic acid template having, in this order: a priming region, a runway region, and an insert region comprising a sequence of interest, wherein the priming region in each of the plurality of polymerase-template complexes comprises a substantially identical sequence, exposing the substrate to a sequencing reaction mixture comprising labeled nucleotides comprising phospholinked labels such that sequencing reactions by the polymerase-template complexes proceed, and observing a time sequence of signals from the labels corresponding to the incorporation of the nucleotide residues of the labeled nucleotides to provide sequence reads comprising sequence data for both the runway region and the insert region, wherein the runway region comprises 200 or more nucleotides.

In certain aspects, the invention provides methods for forming a template having a runway region that comprises providing a circular nucleic acid construct comprising a known double-stranded region having a restriction site, and hairpin adaptors at each end of the double-stranded region connecting the two strands; cleaving the circular nucleic acid construct with a restriction enzyme to form two hairpin adaptors, wherein at least one of the hairpin adaptors has a double-stranded runway region of 200 nucleotides or more and a priming region within the hairpin of the hairpin adaptor; and ligating the hairpin adaptors to a double-stranded nucleic acid insert to form a template nucleic acid having a runway region. In certain embodiments, the cleaving is performed with a restriction enzyme. The length of the runway is optionally between 200 and 2,000 nucleotides, e.g., about 200, 300, 400, 500, or 600 nucleotides. In certain embodiments, the runway region comprises one or more modified bases that are absent from the insert region. Optionally, the one hairpin adaptor comprising the runway region further comprising a barcode region.

In other aspects, methods for real-time single-molecule sequencing of a nucleic acid are provided that comprise providing, on a substrate, a plurality of individually resolvable polymerase-template complexes, each comprising a polymerase enzyme and a template comprising a nucleic acid having, in order: a priming region, a runway region, a barcode region, and an insert region, wherein the priming region and runway region in each of the plurality of polymerase-template complexes has substantially the same sequence, and wherein the plurality of template complexes comprises multiple sub-populations of polymerase-template complexes, each of the sub-populations of polymerase-enzyme complexes having a different barcode region; exposing the substrate to a sequencing reaction mixture comprising labeled nucleotides comprising phospholinked labels such that a sequencing reaction by the polymerase-template complexes is initiated; and observing a time sequence of signals from the labels corresponding to the incorporation of the nucleotide residues of the labeled nucleotides, whereby sequences corresponding to the barcode region and the insert region are determined, whereby the barcode is uniquely identified in 80% of the reads containing the insert sequence.

Also provided are compositions comprising a plurality of polymerase-template complexes, each comprising a polymerase enzyme and a template comprising a nucleic acid having, in this order: a priming region, a runway region comprising 200 or more nucleotides, and an insert region, wherein the priming region and the runway region in each of the plurality of polymerase-template complexes has substantially the same sequence, and wherein the plurality of template complexes comprises multiple sub-populations of polymerase-template complexes, each of the sub-populations of polymerase-enzyme complexes having a different barcode region. Such compositions optionally further comprise a barcode region between the runway region and the insert region. In some embodiments, the template nucleic acid is linear. Optionally or additionally, the runway region, barcode region, and insert region are double-stranded. In certain embodiments, template comprises a double-stranded nucleic acid portion with a hairpin adaptor at one end connecting the two strands, and the priming region is optionally in the hairpin adaptor. In preferred embodiments, the nucleic acid template comprises a double-stranded nucleic acid portion with a hairpin adaptor at each end connecting the two strands, and the two hairpin adaptors (one at each end) can have the same nucleotide sequence or can have different sequences. For example, in some embodiments only one of the hairpin adaptors has a priming site within the hairpin region.

Further, methods are provided for delaying the sequencing of a sequence of interest in a single-molecule, real-time sequencing reaction that comprise initiating a single-molecule, real-time sequencing reaction on a polymerase-template complex, wherein the polymerase-template complex comprises a polymerase enzyme and a nucleic acid template, wherein the nucleic acid template comprises, in order, a priming region, a runway region, and an insert region comprising a sequence of interest, wherein the time from the initiation of the sequencing reactions to the time of sequencing the insert region is greater than about 30 seconds, during which time the polymerase enzyme initiates at the priming region and passes through the runway region. The nucleic acid template preferably comprises a double-stranded region with a hairpin adaptor connecting the strands at an end of the double-stranded region. Optionally, the nucleic acid template comprises two hairpin adaptors, one at each end of the double-stranded region. During the sequencing reactions, the incorporation of nucleotide residues is detected, e.g., optically, electronically or magnetically, and this detection can be accomplished using fluorescence, electrochemistry, capacitance, conductivity, impedance, or a field effect transducer (FET). The runway region is optionally at least 200 nucleotides, and is sometimes greater than 500 nucleotides, and in specific embodiments is between 200 and 2000 nucleotides. In certain embodiments, the runway region comprises one or more modified bases that are absent from the insert region. Preferably, the time from the initiation of the sequencing reactions to the time of sequencing the insert region is greater than about 40, 50, or 60 seconds for a majority of the polymerase-template complexes. Optionally, the nucleic acid templates comprise a barcode region between the runway region and the insert region.

BRIEF DESCRIPTION OF THE DRAWINGS

FIGS. 1(E)-(G) illustrate how the signal over time from these single molecules can be observed.

FIG. 2(A) shows a template having two hairpin adaptors, FIG. 2(B) shows a template having two different hairpin adaptors, FIG. 2(C) shows a template having one hairpin adaptor, FIG. 2(D) shows a linear template.

FIG. 3(A) shows a template having two hairpin adaptors, FIG. 3(B) shows a template having two different hairpin adaptors, FIG. 3(C) shows a template having one hairpin adaptor, FIG. 3(D) shows a linear template.

DETAILED DESCRIPTION OF THE INVENTION

Figure 1:
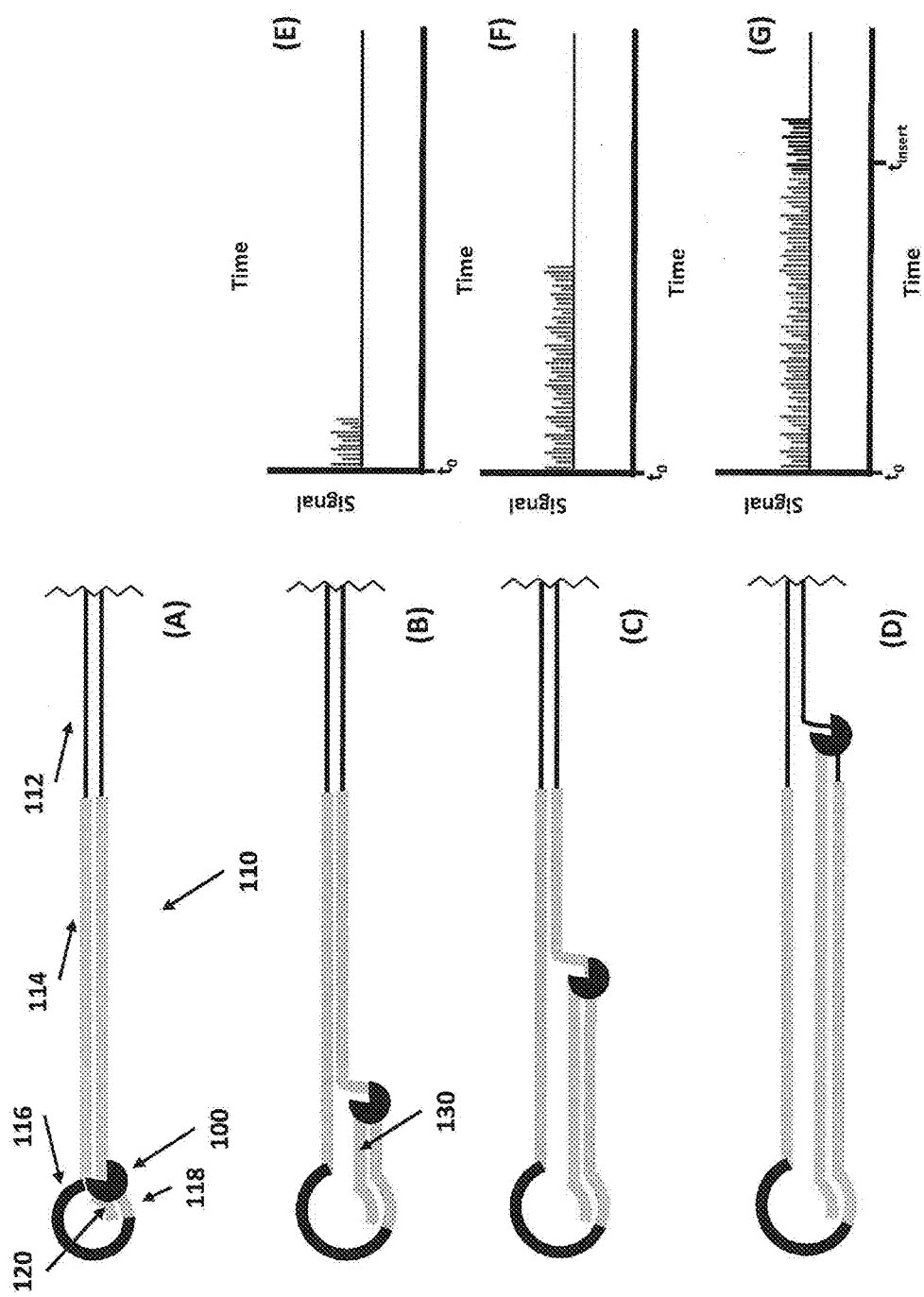
FIG. 1 (A)-(D) shows how the inclusion of a runway region can be used to provide a time delay before sequencing a region of interest in sequencing by synthesis single-molecule, real-time sequencing.

In some aspects, the invention provides methods, compositions, and systems for carrying out nucleic acid sequencing, and in particular single-molecule, real-time sequencing to reliably obtain sequence information for the initial nucleotides in a sequence of interest. Real-time sequencing has a number of advantages over flush-and-scan methods that require repeatedly adding, reading, and washing steps. For example, single-molecule, real-time sequencing by observing the polymerase-mediated incorporation of nucleobases using phosphate-labeled nucleotides can now provide read lengths in the thousands to tens of thousands of nucleotides, read lengths not possible with other technologies. Preferred methods for performing single-molecule, real-time sequencing reactions that benefit from the methods described herein are provided in the art, e.g., in U.S. Pat. Nos. 7,315,019 and 7,056,661; Levene, et al., Science 299:682-686, 2003; Eid et al. Science, 323, 133-138, 2009; Ser. No. 13/914,361 filed Jun. 10, 2013, "Modified Base Detection with Nanopore Sequencing."

In the development of these single-molecule, real-time systems, however, we have found that it can take some time, on the order of tens of seconds to minutes for the sequencing reactions to begin to produce reliable sequencing data. In many cases, this loss of sequencing data for the first portion of the molecule of interest is not a problem. For example, in many cases, sequencing is performed on many overlapping nucleic acid fragments, so the portion of the molecule not sequenced is covered with another fragment. Also, circular constructs are used to carry out sequencing, allowing for repeated sequencing of the same region, in which case the first portion of a molecule not sequenced in a first pass will be adequately covered in subsequent passes.

There are, however, situations in which obtaining a reliable sequence of the initial portion of a molecule of interest is important. One such situation is the sequencing of whole genes or whole transcripts. For these samples, we have found that the population of reads that include both the 3' and the 5' region of the whole gene or transcript are particularly reliable reads for determining the best assembly. Another situation in which reliably sequencing the initial portion of the nucleic acid is important is where barcodes are attached to the initial portion of the sequence. Barcoding can be used, for example, identify which sequence reads correspond to a sub-population of nucleotides in a sample. For example, they can be used to pool multiple patient's samples to be run in a single sequencing reaction. Typical barcode sequences are relatively short sequences, e.g. fewer than 10 bases (although some are longer), that are upstream of the nucleic acid sequence of interest. When such barcodes are used with single-molecule, real-time sequencing, a significant fraction of the barcodes may not be read in cases where reliable sequencing is only obtained after the polymerase has passed a significant portion or all of the barcode region.

A number of approaches have been made to attempt to ensure that all of the sequencing reactions in a single run begin at once, such as hot-start or stage-start methods in which a necessary component is added to initiate of the reaction while the reaction is being monitored. However, even where a single reagent is rapidly delivered to a sequencing chip within the analytical stage, it has been found that it takes tens of seconds to minutes before reliable sequencing is seen. Without being bound by theory, it is generally believed that the reaction must equilibrate before reliable sequence reads can be produced, even though the enzyme becomes active when the hot-start component is added. We describe herein methods and compositions that allow for obtaining reliable sequences of the initial portion of sequences of interest on a high fraction of reads with single-molecule, real-time sequencing.

Runway Regions

In some aspects the invention describes templates having runway regions having lengths of at least 200 nucleotides, at least 500 nucleotides, or at least 1000 nucleotides. We have found that runway sequences with these lengths can provide the delay necessary before sequencing a sequence of interest to ensure that reliable sequence will be obtained. For example, if real-time sequencing can be carried out at an average rate of sequencing of about 3 nucleotides per second, then sequencing a region of about 200 nucleotides will provide a delay on the order of 66 seconds. In some ways, it is counter-intuitive to include such a long runway in a template for a sequencing reaction. For most next-generation sequencing technologies today, the average read length is about 200 bases, so providing a runway sequence of the lengths described herein would be wasting most or all of one's sequencing on known sequence regions, i.e., the runway regions.

In some aspects, the methods of the invention include constructing and sequencing a template molecule having, starting from the 3' end: a priming site, a runway region of 200 or more bases, optionally a barcode region, and an insert containing a nucleic acid sequence of interest or "target" sequence. An insert can be, for example, a genomic nucleic acid fragment, a cDNA molecule, a viral genome, a gene of interest, or any other nucleic acid for which reliable sequence data is sought.

In some cases, the template of the invention is a linear molecule, for example, DNA. While in some cases the invention is described by referring to DNA molecules, it is to be understood that the templates of the invention can comprise any suitable nucleic acid, including RNA, DNA/RNA hybrids, nucleic acids with modified (e.g., methylated, damaged, or missing) bases, and analogs thereof. The template can be double-stranded, single-stranded, or can have both single-stranded and double-stranded portions. Where the template is linear, the runway, optional barcode region, and insert region are typically double-stranded, and at least a portion of the priming site is single-stranded, for example to provide a site for a primer to bind.

In some cases, the template comprises a double-stranded region, and a hairpin at one or both ends. The hairpin at one or both ends connects the two strands of the double-stranded region together. Where a hairpin is present at both ends, the molecule produced is a structurally linear but topologically circular nucleic acid molecule, having no terminal nucleotides. These templates are described in detail in Travers, et al. (2010) Nucleic Acids Research 38:e159; and in U.S. Pat. No. 8,153,375, both of which are incorporated herein by reference in their entireties for all purposes.

FIG. 1 shows how a template comprising a priming region, a runway region, and an insert region with a sequence of interest can be used in order to ensure that the initial portion of the insert sequence is reliably sequenced. FIG. 1(A) shows a polymerase-template complex comprising a polymerase enzyme 100 such as a DNA polymerase, and a template nucleic acid 110, here a DNA template having a double-stranded region comprising an insert region 112, and a runway region 114, and a hairpin 120 connecting the two strands of the double-stranded region. The template has a priming region 118 to which a primer 120 is hybridized, forming a priming initiation site for the polymerase (the 3' end of the primer 120). Here, a primer is used at the priming site, in other cases, a polymerase can be used that can initiate without the need for a primer. In some cases, the priming region for the polymerase can have a nick in one strand of a double-stranded region. Those of skill in the art will appreciate there are many ways to incorporate a priming region into the template nucleic acid, some of which are described in detail in U.S. Published Patent Application 2012/0196279. In FIG. 1(A) the priming site is shown near the end of the hairpin and the beginning of the double-stranded region of the template. The priming site can be anywhere suitable within the hairpin, and in some cases, portions of the hairpin region can be used as part of the runway. In some cases, the priming region can be outside of the hairpin, for example in the double-stranded region of the template.

FIG. 1(B) shows the progress of the polymerase after sequencing has been initiated. The polymerase is a strand-displacing polymerase enzyme that synthesizes a growing ("nascent") strand 130 using the template nucleic acid as a template for synthesis. The polymerase-template complexes are typically localized such that the activity of a single polymerase can be monitored. In some cases, a sequencing-by-synthesis method is used in which the labels of labeled nucleotides are monitored over time to determine the identity of each incorporated nucleobase during synthesis. While FIG. 1 shows the use of the invention in the context of a sequencing-by-synthesis method, any suitable single-molecule sequencing with sufficiently long read lengths can be used with the templates of the invention, including nanopore sequencing (which, in certain embodiments, would use a template having a single hairpin adapter at one end of a double-stranded target region, and an initiation site and runway region at the opposite end of the template, where the initiation site is preferably a single-stranded overhang that is directed into the nanopore). Preferred labels for sequencing by synthesis are phospho-linked labels which are cleaved from the nucleotide as the nucleotide residue (e.g., nucleotide monophosphate comprising a nucleobase, sugar, and phosphate group) is incorporated into the growing chain. The label can be detected prior to cleavage of the label, for example as described by Eid et al. (2009) Science 323:133-138, or can be detected after release as described by Williams et al. (U.S. Pat. No. 6,255,083), which are incorporated herein by reference in their entireties for all purposes herein. Preferred labels are fluorescent labels, but any suitable label including magnetic, electrochemical, capacitive, resistive, or impedance labels can be used. As such, incorporation of nucleotide residues can be detected in a multitude of ways, e.g., electronically, magnetically, or electrochemically; incorporation can be detected using fluorescence, capacitance, conductivity, impedance, or with a field effect transducer (FET).

FIG. 1(E) illustrates how a sequencing reaction is initiated at $t_0$, and signals corresponding to the incorporation of nucleobases over time are observed. We have found that, while there is observable signal after the initiation of the single-molecule sequencing reaction, the sequencing data from this initial region can be unreliable. We have found surprisingly that it can take from tens of seconds to minutes for the quality of the signal to reach a steady-state level. Once the signal reaches this level, the sequencing reaction can provide reliable sequencing data, in some cases for hours. This is particularly significant for arrays of single molecules where tens of thousands to hundreds of thousands of single-molecule sequencing reactions are monitored simultaneously. We believe that part of this sequencing unreliability is due to the time it takes to provide adequate mixing of reagents. For example, in order to provide near simultaneous initiation of the sequencing reactions, one or more sequencing reagent can be withheld, and added to start the reaction. In certain embodiments, where a sequencing reaction is on a substrate or "chip" in a position to be observed (e.g., on a "stage") in a sequencing device, the catalytic metal Mn++ or Mg++ can be added to a chip while it is on the stage, ready to be observed. Even under these circumstances, the initial sequences for tens to hundreds of seconds can be unreliable.

FIG. 1(C) shows a polymerase that has progressed a significant way through the runway region, and FIG. 1(F) shows the corresponding signal versus time. While a significant time may have passed, the signal may not be as reliable as desired.

In FIG. 1(D) the polymerase has extended the growing polymer strand past the runway region and into the insert region. FIG. 1(G) shows the signal versus time, and indicates that at a time $t_{insert}$, the measured signal corresponds to the insert. They runway sequence is a known sequence, allowing for the determination of the point where the sequence of the runway sequence ends and the insert sequence begins. Note that the time $t_{insert}$ will not be a fixed time for all templates, even where the templates have the same length runway. The length of the runway is selected to provide enough time for the reliability of the signal to reach an acceptable level before reaching the insert region. The length of the runway region that is best for a given experiment can be adjusted based on the requirements for the sequencing data. For example, where obtaining adequate mixing is the slow step, the length of the runway region can be adjusted for different mixing conditions and geometries. Another factor that affects the chosen length of the runway region is the average speed of the polymerase. For example, if the polymerase rate is slow, a relatively shorter runway region may be sufficient to provide an appropriate delay time, where a faster polymerase may require a longer runway region. One of skill in the art will understand how to choose the appropriate runway length based on the guidance provided herein.

In some cases, the length of the runway region is at least 200, at least 300, at least 400, at least 500, at least 600, at least 700, at least 800, at least 900, at least 1,000, at least 1,500, or at least 2,000 nucleotides. In some cases, the runway region is chosen to provide at least 10 seconds, at least 20 seconds, at least 30 seconds, at least 40 seconds, at least 50 seconds, at least 60 seconds, at least 90 seconds, at least 120 seconds, at least 180 seconds, at least 240 seconds, at least 360 seconds, at least 480 seconds, before a majority of the single-molecule sequencing reactions reach the initiation region, or point at which processing of the insert or, optionally, barcode sequence begins. In some cases, the runway sequence is chosen to provide reliable sequencing for the first 10 nucleotides of the insert (or barcode, where present) for at least 80%, at least 85%, at least 90%, at least 95%, at least 99% of the reads, where reliable sequencing is defined as the quality of the sequencing of these nucleotides as compared to the quality of sequencing data at the median read length for the sequencing reaction. In some cases, accuracy can be used as a measure of sequencing quality. In some embodiments, acceptable accuracy is at least 85%, 90%, 95%, 98%, or 99%. In other embodiments, acceptable accuracy is less than one error in 10, 20, 30, 40, 50, or 100 bases sequenced.

In some cases, the template comprises a barcode sequence between the runway region and the insert region. The barcode sequence typically provides information to link the insert sequence to a source, and is especially useful in multiplex applications in which nucleic acids from different sources are analyzed in a single reaction volume. The barcode sequence can be used to identify a specific subset of nucleic acid segments in a sample, for example, corresponding to a specific patient or experimental run, or corresponding to a specific targeted nucleic acid region. Where there is a barcode, the length of the runway region can be chosen to be at least 200, at least 300, at least 400, at least 500, at least 600, at least 700, at least 800, at least 900, at least 1,000, at least 1,500, or at least 2,000 nucleotides. In some cases the runway region is chosen to provide at least 10 seconds, at least 20 seconds, at least 30 seconds, at least 40 seconds, at least 50 seconds, at least 60 seconds, at least 90 seconds, at least 120 seconds, at least 240 seconds, at least 360 seconds, at least 480 seconds, before a majority of the single molecule sequencing reactions reach the barcode region. In some cases, the runway region is chosen to identify a unique barcode for at least 80%, at least 85%, at least 90%, at least 95%, at least 99%, of the sequence reads that contain insert region sequences. In certain embodiments, the runway region may comprise multiple, repeated copies of the barcode sequence and be of sufficient length that the reaction is producing reliable sequence data prior to reaching the end of the runway region to capture one or more reliable reads of the barcode sequence prior to entering the insert region. In such embodiments, there is no barcode region separate from the runway region, but the two are combined into one barcode-runway region.

FIG. 2(A) shows a representative template of the invention. The template has a central double-stranded region flanked by two hairpins 216, each hairpin connecting the two strands to form a topologically circular molecule. The template has an insert region 212, which has on either end runway regions 214 and priming regions 218. The specific placement of the regions does not have to be as shown in the figure. For example, priming region 218 can be within the double-stranded region in some cases. This type of template can be formed, for example, by ligating a single type of adaptor to a library of double-stranded nucleotide fragments. The preparation of these types of templates is described for example in U.S. Pat. Nos. 8,153,375 and 8,236,499, which are incorporated by reference for all purposes herein. Typically the insert region comprises the unknown portions of nucleic acid that are being sequenced. The insert region can have, for example, an average length of about 1 kb, about 5 kb, about 10 kb, about 20 kb, about 50 kb, about 100 kb, or more depending on the application and the nucleic acid sample. A typical sample will have fragments of varying lengths resulting in a population of insert regions of varying lengths. This type of template can be sequenced from either side, beginning at the priming region 218 at either end.

FIG. 2(B) shows a template having hairpins at both ends, but having a priming region 218 and runway region 214 on only one side of the template. Here, sequencing can only be initiated from one side of the template. The other hairpin 220 can allow for the sequencing reaction to continue around the hairpin and down the opposite strand, providing for repeated sequencing of the same template. Preparation of these types of templates is described, for example in U.S. Pat. Nos. 8,153, 375 and 8,236,499, which are incorporated by reference for all purposes herein.

FIG. 2(C) shows a template having a priming region 218, runway region 214, and insert region 212, with a hairpin 216 at only one end of the template. The end of the template lacking the hairpin 216 may comprise a blunt end or a single-stranded 5' or 3' overhang. For example, a single-stranded overhang could serve as a priming site, given the correct orientation, or an initiation site for nanopore sequencing where a single-stranded region is inserted into the nanopore to begin the sequencing process.

Figure 2:
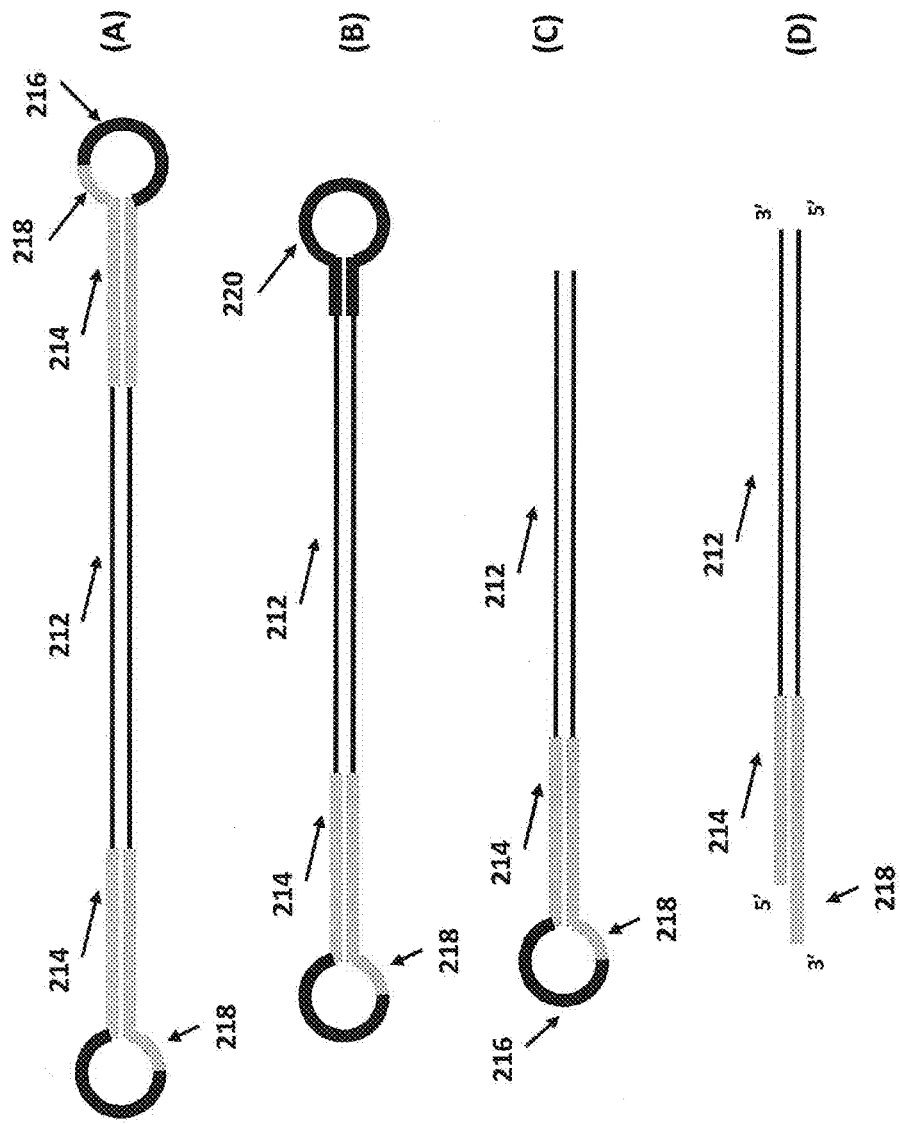
FIG. 2 shows templates of the invention.

FIG. 2(D) shows a linear template having a priming region 218, runway region 214, and insert region 212, with no hairpin. The priming region 218 is typically at least partly single-stranded. Either end of the template may comprise a blunt end or a single-stranded 5' or 3' overhang, which, as noted above, could serve as a priming site or initiation site for nanopore sequencing. Combinations of the features shown for the templates in FIG. 2 can be used.

Figure 3:
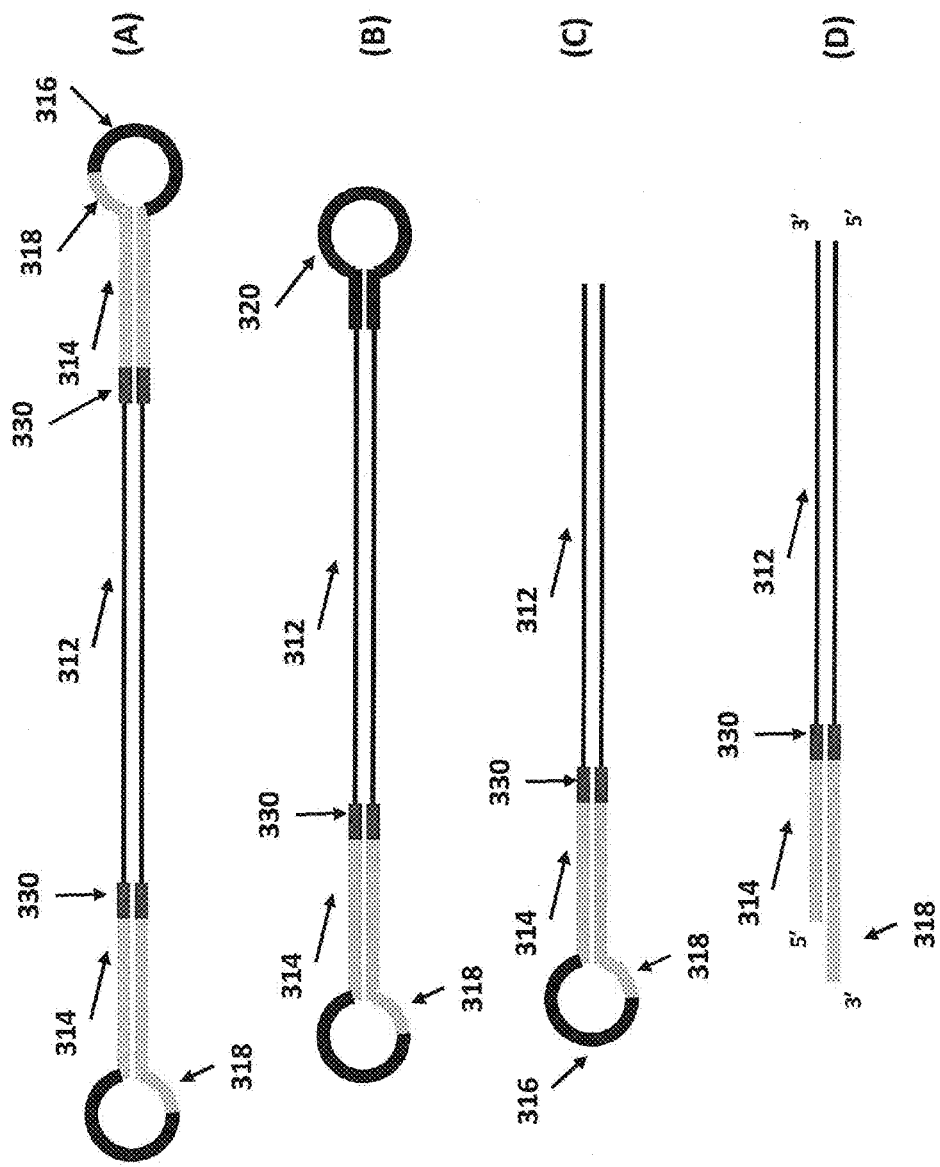
FIG. 3 shows templates of the invention that include barcode regions.

FIG. 3 shows templates similar to those described in FIG. 2, but including barcoding regions. The instant invention is particularly useful with templates having barcodes, wherein it is often important to accurately read the initial portion of a sequencing read, which comprises the barcode sequence, in order to identify the relevant barcode. FIG. 3(A) shows a representative template of the invention. The template has a central double-stranded region flanked by two hairpins 316, each hairpin connecting the two strands to form a topologically circular molecule. The template has an insert region 312, which is connected on either end to barcode regions 330, runway regions 314, and priming regions 318. The specific placement of the regions does not have to be as shown in the figure. For example, priming region 318 can be within the double-stranded region in some cases. A typical sample will have fragments of varying lengths resulting in a population of insert regions of varying lengths. This type of template can be sequenced from either side, beginning at the priming region 318 at either end.

FIG. 3(B) shows a template having hairpins at both ends, but having a barcode region 330, a priming region 318, and runway region 314 on only one side of the template. Here, sequencing can only be initiated from one side of the template. The other hairpin 320 can allow for the sequencing reaction to continue around the hairpin and down the opposite strand, providing for repeated sequencing of the same template. Preparation of these types of templates is described, for example in U.S. Pat. Nos. 8,153,375 and 8,236,499, which are incorporated by reference for all purposes herein.

FIG. 3(C) shows a template having a barcode region 330, a priming region 318, a runway region 314, and an insert region 312, with a hairpin 316 at only one end of the template.

FIG. 3(D) shows a linear template having a barcode region 330, a priming region 318, a runway region 314, and an insert region 312, with no hairpin. The priming region 318 is typically at least partly single-stranded. In some cases, the templates will have other barcodes in addition to the barcodes attached to the initial portion of the insert, for example dispersed throughout the insert, or at the last to be sequenced end of the fragment. There can be multiple barcodes at the initially sequenced end of the insert region.

Typically, the templates of the invention have both known and unknown portions. For example the primer region, runway region, and optional barcode region are generally known sequences, and the insert region has one or more unknown sequences. In some cases, the insert region can have both known and unknown sequences. For example, the insert sequence may have adaptors on one or both ends that are known. Templates of the invention can be made by coupling a known sequence in one or more adaptors, with inserts having unknown sequences. The inserts can comprise a series of fragments with different sequences, and the attachment of adaptors can produce a library of templates. The sequence of the runway can be any sequence that provides the desired delay in sequencing the barcode region and/or insert region, and is preferably identifiable and distinguishable from the insert or barcode sequence. In some embodiments, the runway is a simple sequence, such as a region comprising multiple copies of a short (2-4 bp) sequence, such as a di- or tri-nucleotide repeat. The accuracy of sequencing can be determined along the length of the runway region as the polymerase advances toward the barcode or insert, and the level of accuracy immediately before the polymerase encounters the barcode or insert used to determine the accuracy of the barcode/insert sequences produced. The runway and barcode regions are preferably distinguishable from the barcode or insert regions, respectively. The sequence alone can distinguish, or additional features can be present to distinguish. For example, modified bases known to be absent from the insert sequence can be included in the runway and/or barcode regions. In one example, the insert is amplified DNA, so lacks any methylated bases, and the runway and/or barcode region comprises methylated bases. In another example, the insert is genomic DNA from *C. elegans*, which lacks cytosine methylation, and the runway and/or barcode region comprises methylated cytosines. Other modified bases known in the art are contemplated, as well, e.g., 8-oxoguanosine bases, glucosylated bases, etc., where they are known to be absent from the insert. Likewise, where it is known that an insert comprises a certain type of base modification, that modification can be absent from the runway and/or barcode region. Such modifications can also affect the kinetics of the polymerase enzyme to increase the length of time for the polymerase to reach the insert region, as discussed elsewhere herein.

Figure 4:
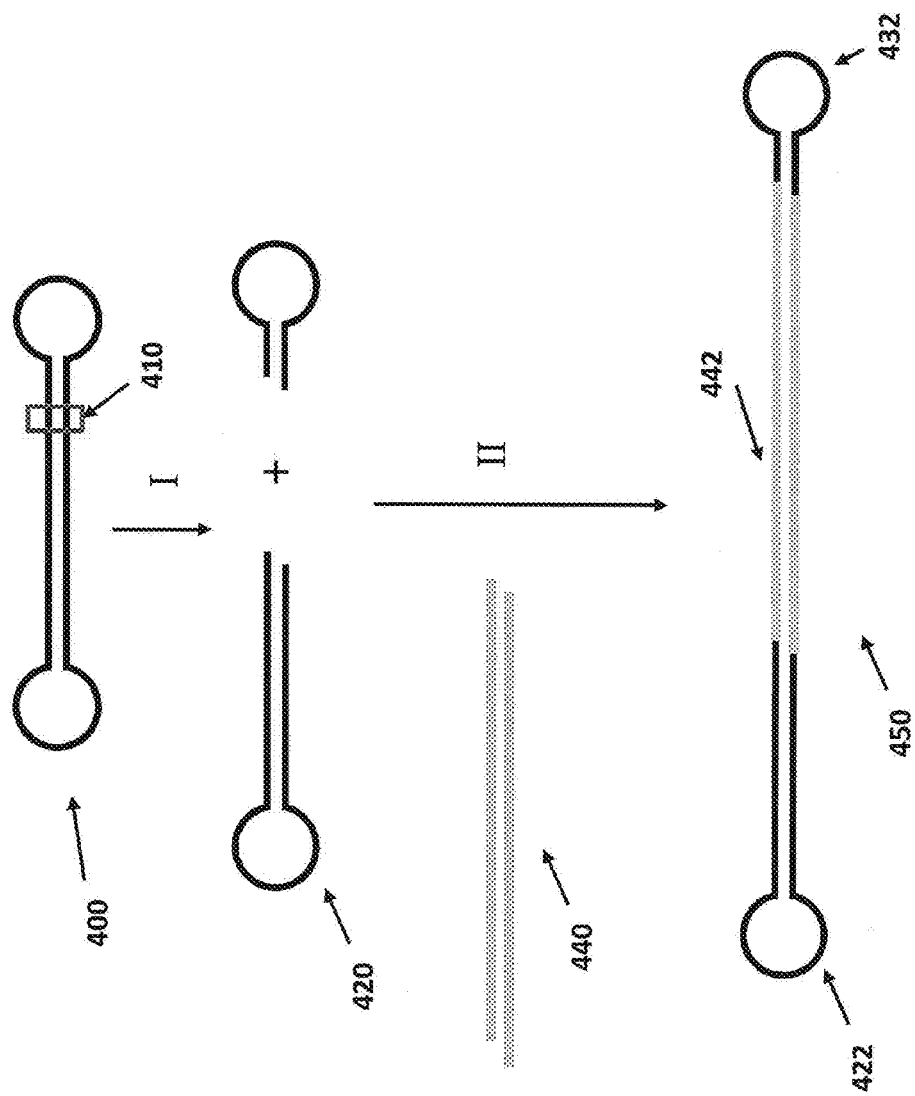
FIG. 4 shows a method for producing a template having a runway region and an insert.

FIG. 4 shows a method for forming a template of the invention. A topologically circular nucleic acid 400, e.g. DNA, is made where the sequence is known. The nucleic acid 400 is produced to have a unique restriction site 410 in a desired portion of the molecule. In step I of FIG. 4, a restriction enzyme is used to specifically cut the nucleic acid 400 to produce hairpin adaptors 420 and 430. By selecting the appropriate restriction enzyme, the sequence of the overhang region can be selected. In step II, the adaptors are ligated onto an insert molecule produced to have the complementary overhangs to the adaptors. A template molecule 450 of the invention having a priming region, and a runway region in adaptor portion 422, and an insert region 442 can be produced. Barcode regions can be introduced from the adaptor, as part of the insert before coupling with the adaptor, or both. Adaptor region 432 can be the same as 422 or different. If 432 is different, it can be chosen not have a priming region, a runway region, or a barcode region. The double-stranded region of the nucleic acid can be, for example from about 200 nucleotides to about 2000 nucleotides in length, or from about 200 nucleotides to about 1000 nucleotides in length. The sequence in the double-stranded region is chosen to be distinguishable from the libraries that will be sequenced using this construct. In some cases, the nucleotides can be made using PCR, synthetic pieces can also be used. Because it is sometimes less expensive and more reliable to produce smaller regions than that desired for the nucleic acid construct, one can ligate together a series of synthetic pieces in order to produce the double-stranded section.

For cutting the nucleic acid construct, blunt cutters are sometimes preferred because they are ready for ligation to end-repaired libraries. Overhang restriction enzymes can also be used, and in some cases, the resulting fragments can be end-repaired to be made blunt. In some cases, palindromic PCR products could be used to generate two identical long hairpin adaptors by cutting in the middle.

Figure 5:
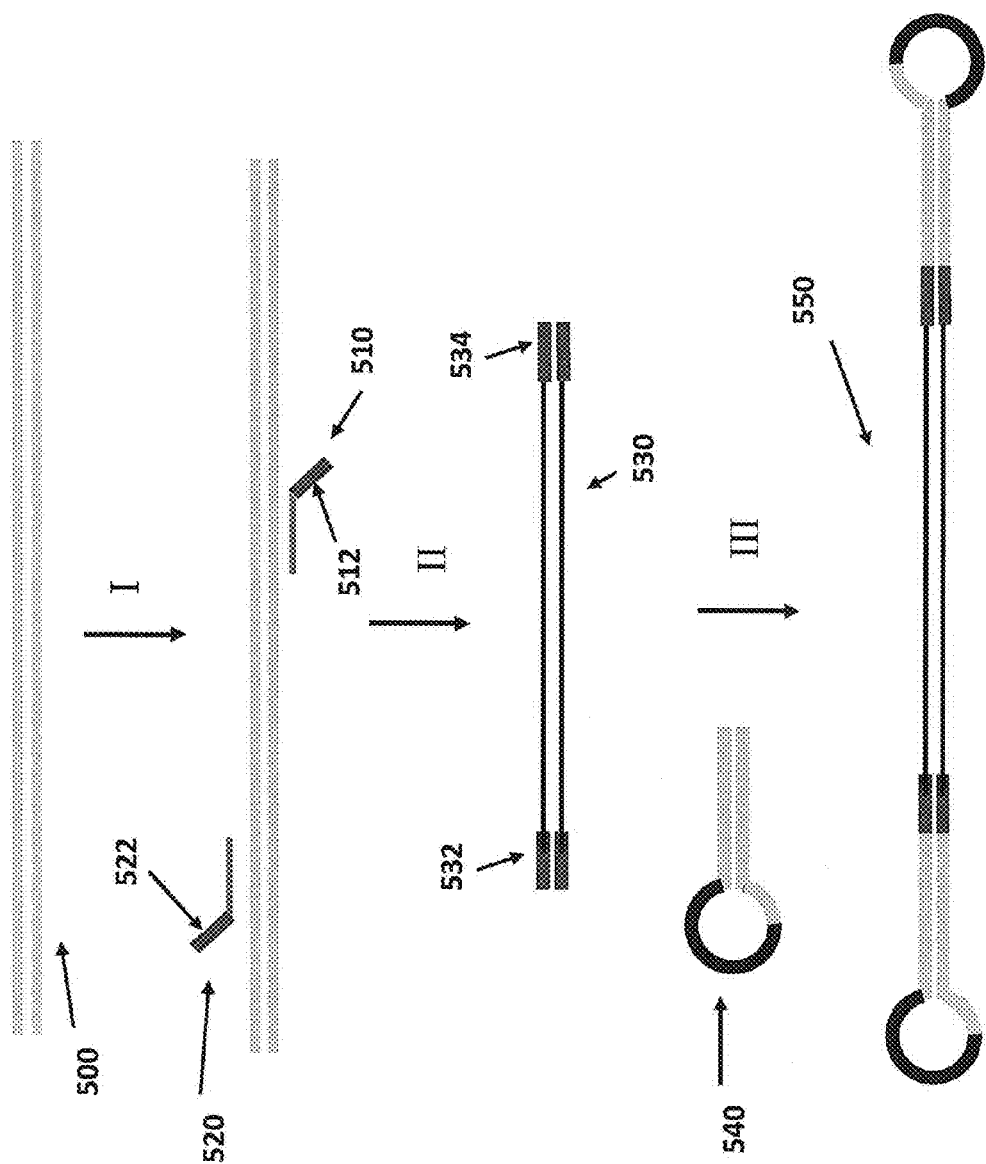
FIG. 5 shows a method to produce a library of templates having runway regions, barcode regions and inserts from a nucleic acid sample using PCR amplification

FIG. 5 shows a method for producing templates of the invention using amplification, for example with polymerase chain reaction (PCR) amplification. In step I, primers 510 and 520 designed to amplify a specific region of the sample nucleic acid 500 are introduced. The primers have tails 512 and 522 with a known sequence that are not complementary to the nucleic acid sample of interest. Amplification (step II) results in amplicons 530 having known sequences 532 and 534 at each end. These known sequences can be used as barcodes for identifying the origin of the amplicon. In step III, adaptors 540 are ligated to the amplicons to produce templates 550.

Figure 6:
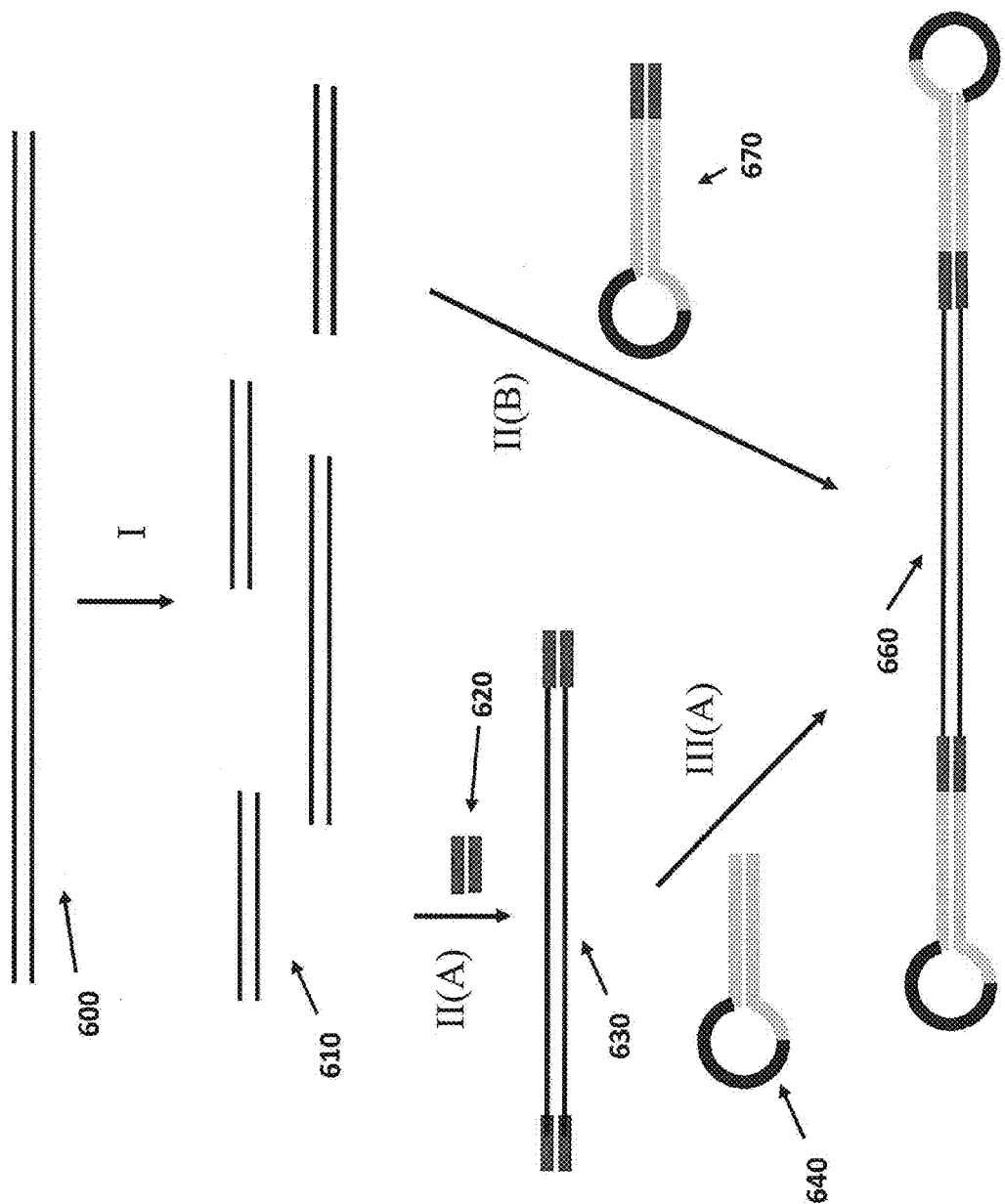
FIG. 6 shows methods for producing a library of templates having runway regions, barcode regions and inserts from a nucleic acid sample using PCR amplification. In method A, barcodes are ligated onto nucleic acid fragments followed by ligation of hairpin adaptors. In method B, a hairpin adaptors having barcodes are ligated onto nucleic acid fragments.

FIG. 6 shows methods for making templates of the invention. A nucleic acid sample 600 is fragmented in step I to produce double-stranded fragments 610. In step II(A), barcode adaptors 620 are ligated onto the fragments producing a library 630 of barcoded fragments. The barcodes on the ends of the library of fragments can be the same or different. The ligation can be either blunt end ligation, or through overlap sequences. In step III(A), adaptors 640 having priming regions and runway regions are ligated onto the fragments to produce templates 660. Step II(B) shows an alternative in which a barcode sequence is on the adaptors 670 that are ligated onto the fragments 610. The methods of A and B can be combined to provide two levels of barcode within the barcode region of the template. As described herein, the templates 660 can have symmetric or asymmetric adaptors, and can have hairpins on both ends one end, or have no hairpins.

Figure 7:
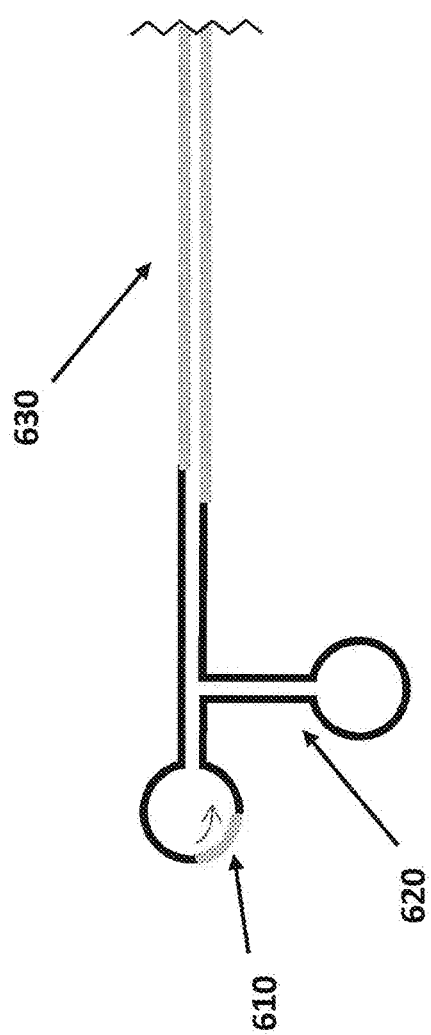
FIG. 7 shows an adaptor that can be used to produce a template having a runway region including a hairpin detour region.

The runway region may be a linear region. In some cases the runway region is not linear. For example, FIG. 7 shows a portion of a template of the invention having a priming region 610, a runway region 620, and an insert region 630. The runway region 620 in the template of FIG. 7 has a secondary structure with a hairpin. In order to sequence the insert region, the polymerase enzyme must sequence through the hairpin portion of the runway region. The use of such structures can provide a relatively long runway in a more compact structure.

In certain embodiments, structural modifications (e.g., modified bases, secondary structure) of an adaptor and/or runway region located between the primer binding site and the barcode or target region slow the rate of incorporation, thereby extending the time prior to sequencing the barcode or target region. In other words, by engineering a "lag" while the polymerase processes such structural modifications prior to reaching the barcode or target region, the likelihood of capturing complete and reliable sequence data is increased. For example, incorporation of complementary nucleobases by a Phi29 polymerase is slowed about five-fold in the presence of 6-mA, and the presence of glucosylated 5-mC slows incorporation of guanine nucleotides about fifty-fold. Other modified bases can also be used, as long as the polymerase is capable of synthesizing past the base with slower kinetics. For example, modified bases that have been shown to affect the kinetics of template-dependent synthesis include, e.g., 5-hydroxymethylcytosine, glucosylated 5-hydroxymethylcytosine, ribonucleotides, N4-methylcytosine, abasic sites, and 8-oxoguanosine. Other modifications that can be used to slow the polymerase enzyme during a synthesis reaction and methods for sequencing them are detailed in Flusberg, et al. (2010) Nature Methods 7:461-465; and U.S. Patent Publication No. 2011/0183320, both of which are incorporated herein by reference in their entireties for all purposes. Modifications to the sugar-phosphate backbone that still allow incorporation, but at a slower rate, are also contemplated (e.g., ribonucleotides or phosphorothioate linkages). Optionally, a plurality of modifications are present between the primer binding site and the barcode or target region, and these modifications can comprise multiple incidences of a single type, different types, or a combination of multiple same and different types of structural modifications. Further, if the modifications are present in the adaptor and they provide enough of a lag of the polymerase, a runway region may not be needed, e.g., since the lag will provide sufficient time for adequate mixing of the reaction components. In other embodiments, both modifications and a runway region are present. For example, an embodiment in which a hairpin (secondary structure modification) is present within a runway region is described supra.

Figure 8:
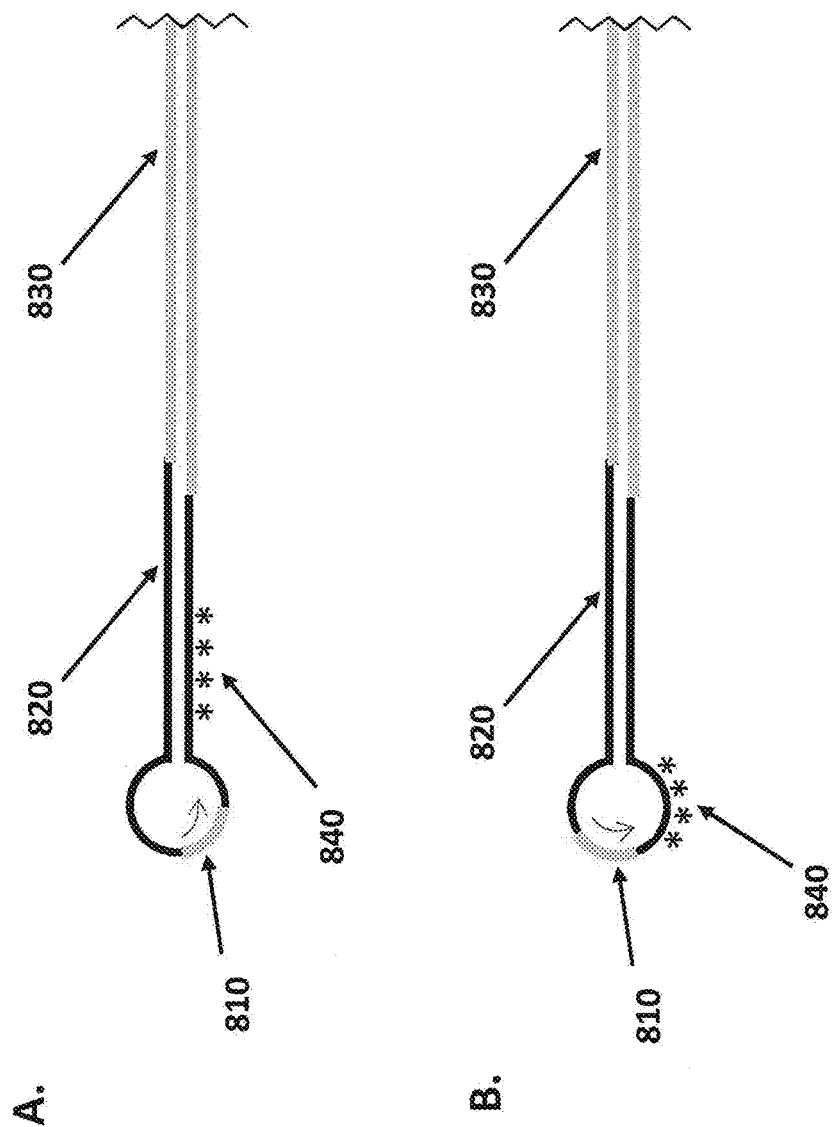
FIG. 8 provides a schematic showing two embodiments for placement of modifications in a template nucleic acid

The modifications can be within or outside of the runway region, or can be present both in the adaptor and runway region. FIG. 8 provides a schematic showing two embodiments of portions of a template of the invention having a priming region 810, a runway region 820, an insert region 830, and modification region 840 for placement of modifications (asterisks) in a template nucleic acid. The top schematic (A) comprises the modification region 840 within the runway region 820 and (B) comprises the modification region 840 in a single-stranded portion of the template between the priming region 810 and the runway region 820. Some modifications, such as abasic sites and other types of DNA damage, are known to cause certain polymerase enzymes to stop primer extension entirely, but a polymerase enzyme capable of synthesizing past such sites after a pause will increase the time before the enzyme encounters a barcode or target region, thereby providing more time for equilibration of the reaction mixture. After the pause, the polymerase continues to perform template-dependent synthesis on the template molecule. Further, the ability of the polymerase to synthesize past a DNA-damage modification is generally helpful when the sample nucleic acids are damaged prior to sequencing, which provides an added benefit to the method. A specific polymerase enzyme capable of synthesizing past abasic sites has been reported in Pastor-Palacios, et al. (2012) PLoS ONE 7(11): e49964, which is incorporated herein by reference in its entirety for all purposes. Further, mutations can be introduced into polymerase enzymes used for sequencing, such as Phi29 to improve modification bypass. In certain embodiments, a DNA-damage modification is an abasic site (e.g., a tetrahydrofuran abasic site), a pyrimidine dimer, or an 8-oxoguanosine. Optionally, more than one modification can be present, e.g., in the adaptor, runway region, or both, and multiple modifications present can be the same type, different types, or a combination thereof. Further, additives to accelerate or slow bypass of the modification can be included in the reaction mixture. The number of modifications and addition of additives that alter the length of the pause can be chosen to ensure the polymerase only reaches the barcode or target region after a length of time that allows sufficient equilibration of the reaction mixture. Further information on using reaction additives to influence the kinetics of a polymerase enzyme is provided, e.g., in U.S. Pat. Nos. 8,133,672 and 8,658,365; and in U.S. Patent Publication Nos. 2014/0206550, 2012/0009567, and 2014/0017674, all of which are incorporated herein by reference in their entireties for all purposes.

In yet further embodiments, a lag is introduced between polymerase initiation and sequencing of a barcode or target region by requiring that the exonuclease activity of a polymerase enzyme (e.g., Phi29 polymerase is one preferred enzyme) cleave a blocking group from the 3'-end of the primer bound to the template prior to beginning template-dependent strand extension. For example, by using a primer having a 3'-terminal dideoxynucleotide, extension is not possible until the dideoxynucleotide is removed by the polymerase exonuclease activity. After removal of the ddNTP, primer extension can proceed. Since the exonuclease activity of the enzyme is not colocalized with the polymerization activity, the primer must be moved from the polymerase site to the exonuclease site for cleavage, and then back again for initiation of synthesis. The time for the transfer from the polymerase site to the exonuclease site can be extended by including modifications within the primer sequence, e.g., phosphorothioate linkages, abasic sites, and modified bases. In particular, a weaker interaction between the primer and the adaptor quickens the transfer and promotes faster cleavage, while stronger interaction slow the transfer and subsequent cleavage, increasing the overall lag time. As such, to create a longer lag time, the primer preferably comprises nucleobases having a stronger interaction with a complementary base than an unmodified, cognate base. For example, 2'-O-methylated oligonucleotides, PNAs, LNAs, and other tighter-binding modified bases can be included in the primer to strengthen the binding between the primer and the adaptor. Another benefit to using these tighter-binding nucleotides in the primer is that the binding is more stable once the primer finds the primer-binding site in the adaptor, which facilitates polymerase complex formation (i.e., binding of the polymerase enzyme to the primer-template complex). In addition, internal phosphorothioate linkages provide the added benefit of preventing excessive cleavage by the exonuclease activity since these bonds are not cleavable by the enzyme. A 3'-blocked primer can be used as the only mechanism for extending the time period between polymerase binding and sequencing of a barcode or target region, or can be used in combination with any of the other methods described herein, e.g., use of a runway, modifications, etc.

Single Molecule Sequencing

The methods compositions and systems of the invention can be used for single-molecule sequencing of nucleic acids in real time. Such methods include sequencing-by-synthesis methods, as well as sequencing by exonuclease cleavage and nanopore sequencing, e.g., where a single-stranded template is passed through a nanopore to detect its constituent base sequence. For sequencing processes that rely upon monitoring of the incorporation of nucleotides into growing nascent strands being synthesized by the complex, the progress of the reaction through these steps is of significant importance. In particular, for certain "real time" nucleotide incorporation monitoring processes, the detectability of the incorporation event is improved based upon the amount of time the nucleotide is bound to and retained within the synthesis complex during the ultimate incorporation of its constituent nucleobase into a primer extension product.

By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, 2003, and Eid et al. Science, 323, 133-138, 2009, the full disclosures of which are incorporated herein by reference in their entireties for all purposes.

Figure 9:
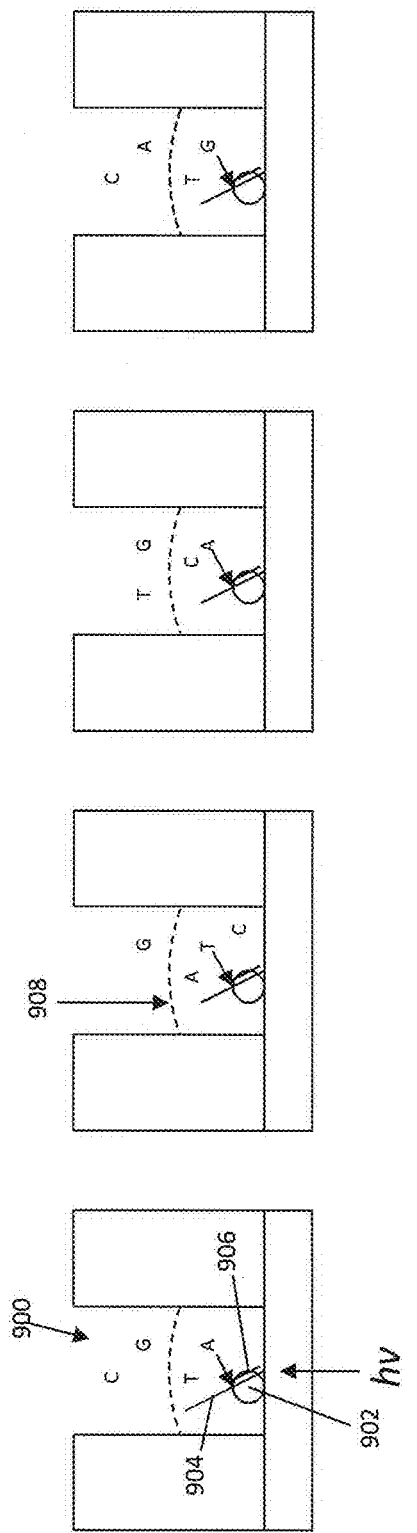
FIG. 9 shows a schematic illustration of performing sequencing within an optical confinement.

In an exemplary technique, as schematically illustrated in FIG. 9, a nucleic acid synthesis complex, including a polymerase enzyme 902, a template sequence 904 and a complementary primer sequence 906, is provided immobilized within an observation region 900, that permits illumination (as shown by hv) and observation of a small volume that includes the complex without excessive illumination of the surrounding volume (as illustrated by dashed line 908). By illuminating and observing only the volume immediately surrounding the complex, one can readily identify fluorescently labeled nucleotides that are used by the polymerase enzyme to incorporate nucleobases during that synthesis, as such nucleotides are retained within that observation volume by the polymerase for longer periods than those nucleotides that are simply randomly diffusing into and out of that volume.

In particularly preferred exemplary systems, the confined illumination volume is provided through the use of arrays of optically confined apertures termed zero-mode waveguides, e.g., as shown by confined reaction region 900, (ZMWs)(See, e.g., U.S. Pat. No. 6,917,726, which is incorporated herein by reference in its entirety for all purposes). For sequencing applications, the DNA polymerase is typically provided immobilized upon the bottom of the ZMW (See, e.g., Korlach et al., PNAS U.S.A. 105(4): 1176-1181. (2008), which is incorporated herein by reference in its entirety for all purposes.)

In operation, the fluorescently labeled nucleotides or nucleotide analogs (shown as A, C, G and T) bear one or more fluorescent dye groups on a phosphate moiety that is cleaved from the nucleotide upon incorporation, e.g., a terminal phosphate, and or one or more fluorescent dye groups whose removal by a selective cleaving activity will allow for further incorporation events. As a result of the cleavage and release of the labels, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al., Nucleosides, Nucleotides and Nucleic Acids, 27:1072:1083, 2008.

In another exemplary technique, the immobilized complex and the nucleotides to be incorporated are each provided with interactive labeling components. During binding and incorporation, the nucleotide-borne labeling component is brought into sufficient proximity to the complex-borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

Delayed Illumination

In a further aspect, methods for delaying real-time sequencing can comprise delaying the initiation of illumination of the ongoing polymerase reaction. Illumination, which typically begins prior to initiation, can instead commence after a period of time following initiation. Since the early data is typically not reliable for base calling, illumination of the reaction can be delayed until a later time that is preferably before the polymerase reaches the end of the runway region and begins to pass through the barcode (if present) and insert region. By delaying illumination, the sequence data collected after illumination begins is more likely to be useful for barcode identification and base calling of the insert sequence. In this way, the average quality of the resulting sequence read is improved due to the absence of early, low-quality sequence data. Further, the presence of excitation illumination has been linked to photo-induced damage of various components in the reaction, so minimizing the amount of time the reaction is illuminated prior to collection of sequence data may reduce such damage, thereby extending the time during which the reaction is generating high-quality sequence data. The length of the delay is dependent on the kinetics of the polymerase used and the length of the runway region. Since the average rate of a given polymerase is known or easily discoverable to the ordinary practitioner, and the runway region is also known, it requires only a simple calculation to determine how long to wait before beginning to illuminate the reaction. For example, if the polymerase has a rate of one base per second, and the runway region is 500 base pairs in length, it will take about 500 seconds for the polymerase to reach the barcode/insert region. Since there is some variability in polymerase rates, the ordinary practitioner is advised to ensure illumination begins before the polymerase reaches the barcode/insert region. As such, in this example, a delay of 450 seconds would be a reasonable delay that is likely to capture sequence data from the illuminated reaction prior to the polymerase reaching the barcode/insert region, assuming a relatively low variability in the rate of the polymerase enzyme.

In alternative embodiments, delayed illumination can be used during sequencing of a barcoded, double-stranded template comprising hairpin adapters on both ends, such that illumination does not begin until the polymerase has completely or nearly completely traversed the first strand of the duplex. As such, no or very little sequence data is generated for the first pass of the polymerase through the insert region, but the presence of the hairpin adapters allows the polymerase to continue around one adapter and process the second strand, and potentially proceed around the second adapter to generate sequence data for the first strand. This method is especially useful where the template does not comprise a true runway region before the barcode, per se, and the passage through the first strand of the duplex essentially functions as a runway region prior to passage through the barcode and insert sequence, e.g., in the second strand. As such, the invention provides a method of performing sequencing by synthesis in which initiation is performed in the absence of illumination and the polymerase progresses for a desired distance such that it is through or nearly through the first strand before illumination is initiated. For templates having only one barcode region adjacent to the insert region, this strategy increases the probability that the polymerase will be producing high-quality sequence data when it first encounters the barcode during illumination, whether the encounter takes place on the second strand and/or on the first strand but at the end distal from the polymerase start site. For templates having barcode regions flanking the insert region, this strategy increases the probability that the polymerase will first encounter the distal barcode on the first strand and/or the distal barcode on the second strand during production of high-quality sequence data. Similar to methods using delayed illumination in the presence of a runway region, the length of time the reaction proceeds absent illumination depends on the rate of polymerization and the length of the barcode/insert region.

Although use of a duplex template having hairpins at both ends is recommended to allow for sequencing of the first strand after illumination begins, it is not required. In some embodiments, the template comprises only one hairpin at the end distal to the start site of the polymerase. The polymerase initiates synthesis in the dark and proceeds through or nearly through the first strand before initiation of illumination. The polymerase continues synthesis through the barcode and insert on the second strand, stopping at the 5' end.

Figure 10:
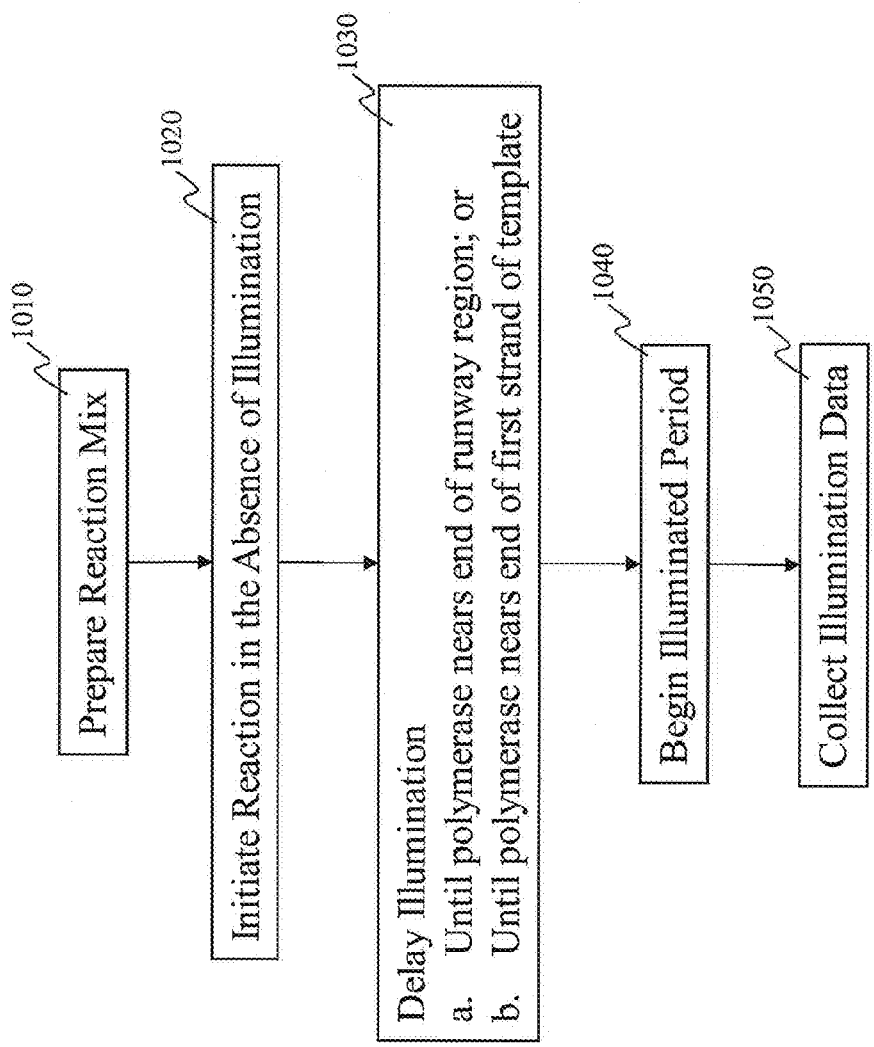
FIG. 10 provides a flow diagram outlining a method for delaying sequence data collection by delaying illumination of a sequencing reaction.

FIG. 10 provides a general flow of certain embodiments of the methods for delaying sequencing that comprise delayed illumination. In step 1010, the reaction mixture is prepared, and in step 1020, the reaction is initiated in the absence of illumination. In step 1030, the reaction is carried out in the absence of illumination and the initiation of illumination is delayed until a time at which the polymerase is either nearing the end of a runway region or nearing the end of the first strand of a duplex template prior to a barcode region either at the distal part of the first strand or on the second strand. Illumination is initiated at step 1040 and high-quality reaction data is collected for the remainder of the reaction at step 1050.

In certain aspects, the instant method provides a strategy for not monitoring a reaction during a period in which low-quality data is being produced, and initiating monitoring when high-quality data is expected to be generated. In additional aspects, the instant method provides a strategy for delaying illumination of a sequencing reaction until the polymerase enzyme is producing high-quality sequence data and, optionally, is nearing a barcode region. In further aspects, the instant method provides a strategy for producing a sequence read of higher average quality than would be produced if the reaction were carried out entirely while being illuminated and monitored, since the non-illuminated period prevents low-quality sequence data from being collected and added to the sequence read produced during the high-quality data production.

Further methods for controlling illumination periods during an analytical reaction are provided, e.g., in U.S. 2014/0134629, which is incorporated herein by reference in its entirety for all purposes.

Polymerase Enzymes

Polymerase enzymes having labels indicative of polymer conformation can include polymerases mutated to have desirable properties for sequencing. For example, suitable enzymes include those taught in, e.g., WO 2007/076057, WO 2008/051530, and U.S. patent application Ser. No. 12/584,481 filed Sep. 4, 2009. The modified polymerases may have modified properties such as (e.g., decreased branch fraction formation, improved specificity, improved processivity, altered rates, improved retention time, improved stability of the closed complex, etc.).

In addition, the polymerases can be further modified for application-specific reasons, such as to increase photostability, e.g., as taught in U.S. patent application Ser. No. 12/384,110 filed Mar. 30, 2009, to improve activity of the enzyme when bound to a surface, as taught, e.g., in WO 2007/075987, and WO 2007/076057, or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

DNA Polymerases

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/ xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287.

RNA Polymerases

In some embodiments, the polymerase enzyme that is used for sequencing is an RNA polymerase. Any suitable RNA polymerase can be used including RNA polymerases from bacteria, eukaryotes, viruses, or archea. Suitable RNA polymerases include RNA Pol I, RNA Pol II, RNA Pol III, RNA Pol IV, RNA Pol V, T7 RNA polymerase, T3 RNA polymerase, Phi6 RNA replicase, or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors.

There are many proteins that can bind to RNAP and modify its behavior. For instance, GreA and GreB from E. coli and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e. they help RNAP choose whether or not to express certain genes. RNA dependent RNA polymerases (RNA replicases) may also be used including viral RNA polymerases: e.g. poliovirus 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or systems of the invention include RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA-dependent DNA polymerases, DNA-dependent RNA polymerases, RNA-dependent DNA polymerases (reverse transcriptases), and RNA-dependent RNA polymerases.

Reaction Conditions

The reaction conditions used can influence the relative rates of the various reactions. Thus, controlling the reaction conditions can be useful in ensuring that the sequencing method is successful at calling the bases within the template at a high rate. For example, the reaction conditions can be chosen to be used with templates of the invention having the desired length of runway region. The reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors. Manipulation of reaction conditions to achieve or enhance two slow step behavior of polymerases is described in detail in U.S. patent application Ser. No. 12/414,191 filed Mar. 30, 2009, and entitled "Two slow-step polymerase enzyme systems and methods."

Enzymatic reactions are often run in the presence of a buffer, which is used, in part, to control the pH of the reaction mixture. The type of buffer can in some cases influence the kinetics of the polymerase reaction in a way that can lead to two slow-step kinetics. For example, in some cases, use of TRIS as buffer is useful for obtaining a two slow-step reaction. Suitable buffers include, for example, TAPS (3-{[tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a reaction exhibiting two-slow-step kinetics. The pH can be adjusted to a value that produces a two-slow-step reaction mechanism. The pH is generally between about 6 and about 9. In some cases, the pH is between about 6.5 and about 8.0. In some cases, the pH is between about 6.5 and 7.5. In some cases, the pH is about 6.5, 6.6, 6.7, 6.8, 6.9, 7.0, 7.1, 7.2, 7.3, 7.4, or 7.5.

The temperature of the reaction can be adjusted to ensure that the relative rates of the reactions are occurring in the appropriate range. The reaction temperature may depend upon the type of polymerase or selective cleaving activity, such as an exonuclease, that is employed. Temperatures between 15° C. and 90° C., between 20° C. and 50° C., between 20° C. and 40° C., or between 20° C. and 30° C. can be used.

In some cases, additives can be added to the reaction mixture that will influence the kinetics of the reaction. In some cases, the additives can interact with the active site of the enzyme, acting for example as competitive inhibitors. In some cases, additives can interact with portions of the enzyme away from the active site in a manner that will influence the kinetics of the reaction. Additives that can influence the kinetics include, for example, competitive but otherwise unreactive substrates or inhibitors in analytical reactions to modulate the rate of reaction as described in copending U.S. Utility patent application Ser. No. 12/370,472, the full disclosure of which is incorporated herein by reference in its entirety for all purposes.

One aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interaction in polymerase reactions, see, e.g., Arndt, et al., Biochemistry (2001) 40:5368-5375. Suitable conditions include those described in U.S. patent application Ser. No. 12/384,112, filed Mar. 30, 2009.

Template Nucleic Acids

The template nucleic acids of the invention can comprise any suitable polynucleotide, including double-stranded DNA, single-stranded DNA, single-stranded DNA hairpins, DNA/RNA hybrids, RNAs with a recognition site for binding of the polymerizing agent, RNA hairpins, and combinations thereof. Further, target polynucleotides may be a specific portion of a genome of a cell, such as an intron, regulatory region, allele, variant or mutation; the whole genome; or any portion thereof. In other embodiments, the target polynucleotides may be mRNA, tRNA, rRNA, ribozymes, antisense RNA or RNAi.

The template nucleic acids of the invention can include modified bases, such as methylcytosine, hydroxymethylcytosine, methyladenine, and damaged bases. The template nucleic acids of the invention can include unnatural nucleic acids such as PNAs, modified oligonucleotides (e.g., oligonucleotides comprising nucleotides that are not typical to biological RNA or DNA, such as 2'-O-methylated oligonucleotides), modified phosphate backbones and the like. Likewise, primers used in the methods herein may also comprise either naturally modified bases or unnatural nucleic acids. For example, some primers comprising modified bases (e.g., 2'-O-methylated nucleotides) exhibit stronger hybridization as compared to primers having only canonical bases, and the stronger binding can benefit hybridization of the primer to a template nucleic acid.

Nucleotide Analogs

Where sequencing-by-synthesis methods are used, the type of nucleotide analog that is incorporated can be important. The nucleotide analogs for use in the invention can be any suitable nucleotide analog that is capable of being a substrate for the polymerase and for the selective cleaving activity. It has been shown that nucleotides can be modified and still used as substrates for polymerases and other enzymes. Where a variant of a nucleotide analog is contemplated, the compatibility of the nucleotide analog with the polymerase or with another enzyme activity such as exonuclease activity can be determined by activity assays. The carrying out of activity assays is straightforward and well known in the art.

The nucleotide analog can be, for example, a nucleoside polyphosphate having three or more phosphates in its polyphosphate chain with a label on the portion of the polyphosphate chain that is cleaved upon incorporation into the growing strand, the nucleoside polyphosphate also having a label on a 3' hydroxyl leaving group. The labeled leaving group on the 3' hydroxyl is subsequently cleaved by an enzyme such as an exonuclease. The polyphosphate can be a pure polyphosphate, e.g. —O—PO3-, or the polyphosphate can include substitutions. For example, one or more of the linking oxygens in the polyphosphate can comprise an S, an NH or an NR group, where R is a substituted or unsubstituted alkyl group. R can act as a place on the polyphosphate for including functionality for improved binding of the nucleotide, or can provide a place for attaching a label, with or without a linker.

Systems

The invention includes systems for sequencing of nucleic acid templates. The systems provide for concurrently sequencing a plurality of nucleic acid templates. The system can incorporate all of the reagents and methods described herein, and provides the instrumentation required for containing the sample, illuminating the sample with excitation light, detecting light emitted from the sample during sequencing to produce intensity-versus-time data from the labeled nucleotides and from the label indicative of enzyme conformation, and determining the sequence of a template using the intensity-versus-time data.

The system for sequencing generally comprises a substrate having a plurality of single polymerase enzymes, single templates, or single primers bound to the surface. In the case of a highly processive enzyme polymerase complexes each comprising a polymerase enzyme, a nucleic acid template, and a primer are immobilized. The sequencing reagents generally include two or more types of nucleotide analogs, each nucleotide analog labeled with a different label. The polymerase sequentially adds nucleotides or nucleotide analogs to the growing strand, which extends from the primer. Each added nucleotide or nucleotide analog is complementary to the corresponding base on the template nucleic acid, such that the portion of the growing strand that is produced is complementary to the template.

For fluorescent labels, the system comprises illumination optics for illuminating the enzyme complexes. The illumination optics illuminate the complexes in a wavelength range that will excite the labels on the nucleotides or nucleotide analog and which will excite the labels on the polymerase enzyme that are sensitive to changes in conformation.

For optical detection the system comprises detection optics for observing signals from the labeled nucleotides or nucleotide analogs and signals from the labeled enzyme during the enzyme mediated addition. The detection optics observe a plurality of single polymerase enzyme complexes concurrently, observing the nucleotide or nucleotide analog additions for each of them. For each of the observed polymerase enzyme complexes, the detection optics concurrently observe the signals from each of the labeled nucleotides or nucleotide analogs and the signals from the labeled enzyme that are indicative of enzyme conformation.

The system also comprises a computer configured to determine the type of the nucleotide or nucleotide analog that is added to the growing strand using the observed signal from the label of the nucleotide or nucleotide analogs; whereby observed signals from the labeled polymerase enzyme are used to indicate whether a type of nucleotide or nucleotide analog is incorporated into the growing strand. The computer generally receives information regarding the observed signals from the detection optics in the form of signal data. The computer stores, processes, and interprets the signal data, using the signal data in order to produce a sequence of base calls. The base calls represent the computers estimate of the sequence of the template from the signal data received combined with other information given to the computer to assist in the sequence determination.

Figure 11:
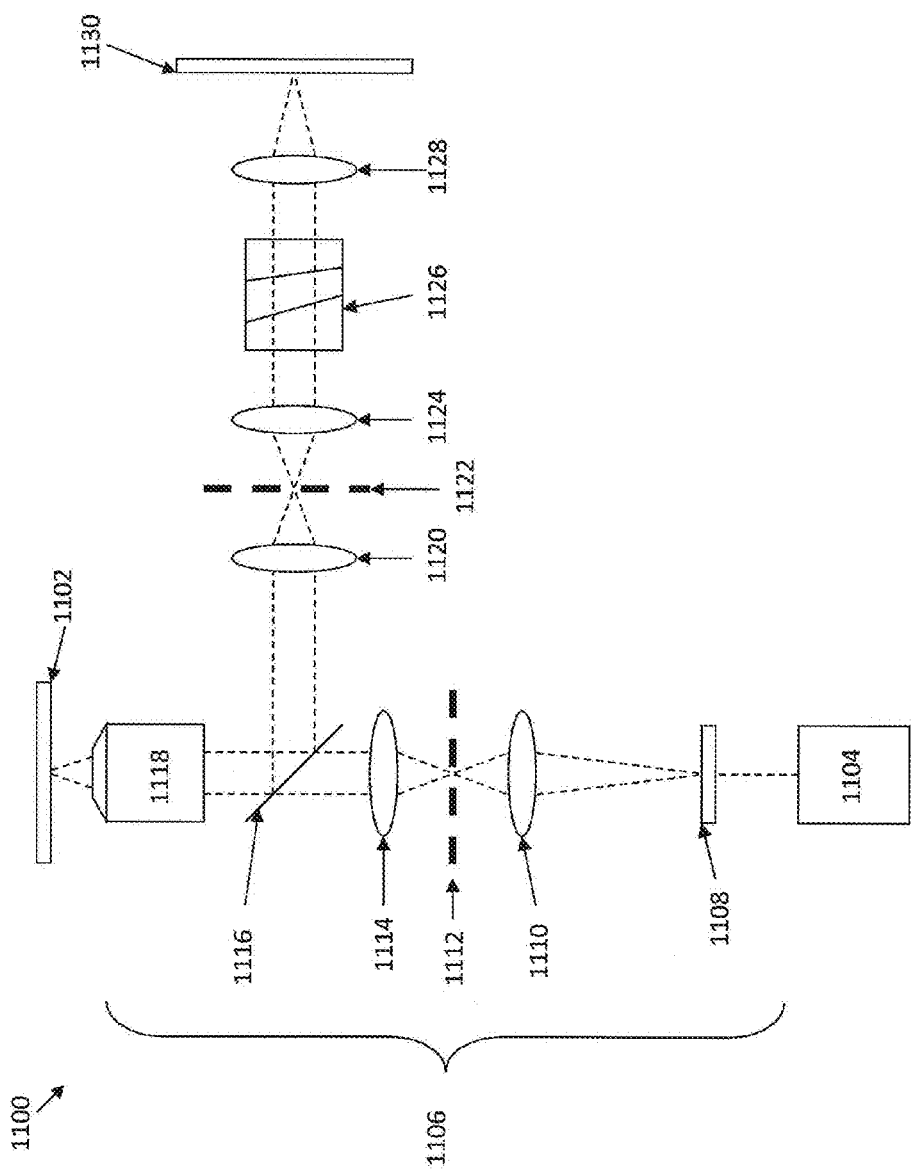
FIG. 11 shows an embodiment of a system of the invention for carrying out single molecule sequencing.

One example of such system is illustrated in FIG. 11. As shown, the system 1100, includes a reaction array, such as a zero-mode waveguide array 1102 upon which a number of discrete reaction regions are arrayed. Within the zero-mode waveguides are immobilized single polymerase enzyme complexes, single templates or single primers having labels indicative of enzyme conformation. The zero-mode waveguides are also exposed to sequencing reagents including labeled nucleotides or nucleotide analogs, for example four differentially labeled nucleotides or nucleotide analogs. In the case of a zero-mode waveguide array, large numbers of zero-mode waveguides are typically provided arrayed in rows and columns on the substrate. Within the various ZMWs are provided reactants of interest for a given analysis. For example, in the context of nucleic acid sequencing by synthesis, a sequencing complex that includes a template nucleic acid sequence, a complementary primer sequence, a nucleic acid polymerase enzyme, and a reaction mixture of nucleotide analogs required for primer extension are provided with the ZMW. ZMW arrays can be fabricated at ultra-high density, providing anywhere from 1100 ZMWs per cm$^2$, to 1,000,000 ZMWs per cm$^2$, or more. Thus, at any given time, it may be desirable to analyze the reactions occurring in from 100, 1000, 3000, 5000, 10,000, 20,000, 50,000, 100,000 or 1 Million, 10 Million or more ZMWs or other reaction regions within a single analytical system or even on a single substrate.

As shown in FIG. 11, the system includes a source of excitation radiation for exciting fluorescent reactants in the reaction regions, such as laser 1104. An optical train 1106 delivers excitation radiation from laser 1104 to the ZMW array or substrate 1102. The optical train also collects fluorescent signals from the various ZMWs on the array, and conveys those signals to a detector, such as EMCCD 1130. The optical train 1106 includes a multiplex component, such as diffractive optical element (DOE) 1108 (also referred to as a holographic optical element or HOE), that converts a single excitation beam to large number of discrete excitation beams that will be targeted in an array of illumination spots that correspond to the location of the ZMWs on the array 1102. The multiple beams are passed through a dichroic 1116 that is selected to pass excitation light and reflect the fluorescence from the array 1102. Prior to passing through the dichroic 1116, the illumination beams may be passed through a confocal filter 1112 which may have associated with it a pair of focusing lenses, e.g., lenses 1110 and 1114, in order to focus these beams through the confocal pinhole(s). The excitation light that is passed through dichroic 1116 is then focused in a targeted pattern onto the plane of the array 1102 via objective lens 1118.

Fluorescent signals from array 1102 are then collected by the objective lens 1118, and passed to dichroic 1116, which reflects the fluorescent signals toward detector 1130. The signals from the discrete ZMWs on the array are then passed through a spatial filter, such as confocal mask 1122, to reduce background noise, such as photoluminescence, out of focal plane autofluorescence or scattered light, which again typically has associated with it a pair of focusing lenses, e.g., lenses 1120 and 1124. The signals can then be passed through a dispersive optical element, such as wedge prism 1126, that differentially directs light of differing spectral characteristics, allowing for distinction of different fluorescent signals based upon the location upon the detector, upon which they impinge. The differentially directed signal components are then directed through additional focusing optics, e.g., focusing lens 1128, and ultimately impact the EMCCD detector 1130. As noted, the position on the detector upon which a given signal is incident can then be indicative of (1) the originating ZMW in the array, and (2) the spectral characteristics of the signal component, which is used, for example, to identify the type of fluorescently labeled nucleotide analog incorporated in an extension reaction and that is used to monitor the label on the enzyme which is indicative of enzyme conformation.

Optical illumination and detections systems which can be used with the present invention are described, for example in U.S. patent application Ser. No. 12/351,173, filed Jan. 9, 2009; Ser. No. 11/901,273, filed Sep. 14, 2007; Ser. No. 12/151,979, filed May 9, 2008; Ser. No. 12/079,944, filed Mar. 27, 2008; Ser. No. 11/849,157, filed Aug. 31, 2007; Ser. No. 12/560,308, filed Sep. 15, 2009; and Ser. No. 13/031,103, filed Feb. 18, 2011, which are incorporated herein by reference for all purposes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as PEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

Optical Confinements—Zero-Mode Waveguides

In some embodiments of the methods and systems of the invention, optical confinements are used to enhance the ability to simultaneously observe multiple complexes, each comprising a single polymerase enzyme. In general, optical confinements are disposed upon a substrate and used to provide electromagnetic radiation to or derive such radiation from only very small spaces or volumes. Such optical confinements may comprise structural confinements, e.g., wells, recesses, conduits, or the like, or they may comprise optical processes in conjunction with other components, to provide illumination to or derive emitted radiation from only very small volumes. Examples of such optical confinements include systems that utilize, e.g., total internal reflection (TIR) based optical systems whereby light is directed through a transparent portion of the substrate at an angle that yields total internal reflection within the substrate.

The substrates of the invention are generally rigid, and often planar, but need not be either. Where the substrate comprises an array of optical confinements, the substrate will generally be of a size and shape that can interface with optical instrumentation to allow for the illumination and for the measurement of light from the optical confinements. Typically, the substrate will also be configured to be held in contact with liquid media, for instance containing reagents and substrates and/or labeled components for optical measurements.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

In accordance with the invention, arrays of confinements, e.g., zero-mode waveguides, are provided in arrays of more than 100, more than 1000, more than 10,000, more than 100,000, or more than 1,000,000 separate waveguides on a single substrate. In addition, the waveguide arrays typically comprise a relatively high density of waveguides on the surface of the substrate. Such high density typically includes waveguides present at a density of greater than 10 zero-mode waveguides per $mm^2$, preferably, greater than 100 waveguides per $mm^2$ of substrate surface area, and more preferably, greater than 500 or even 1000 waveguides per $mm^2$ and in many cases up to or greater than 100,000 waveguides per mm $mm^2$. Although in many cases, the waveguides in the array are spaced in a regular pattern, e.g., in 2, 5, 10, 25, 50 or 100 or more rows and/or columns of regularly spaced waveguides in a given array, in certain preferred cases, there are advantages to providing the organization of waveguides in an array deviating from a standard row and/or column format. In preferred aspects, the substrates include zero-mode waveguides as the optical confinements to define the discrete reaction regions on the substrate.

The optical confinements can be zero-mode-waveguides. Zero-mode waveguides have been described in, e.g., U.S. Pat. Nos. 6,917,726 and 7,315,019, the full disclosures of which are incorporated herein by reference in their entireties for all purposes. Generally, such waveguides comprise a core disposed through a cladding layer, which in the case of applications to reactions, comprises an aperture disposed through the cladding layer that can receive the reactants to be monitored. Typically, the aperture has at least one cross-sectional dimension, e.g., diameter, which is sufficiently small that light entering the waveguide is prevented in some measure from propagating through the core, effectively resulting in a very small portion of the core and its contents being illuminated, and/or emitting optical signals that exit the core. In the case of optical signals (and excitation radiation), the waveguide cores will typically be between about 1 nm and about 300 nm, between about 10 and about 200 nm, or between about 50 and about 150 inn in diameter where light in the visible range is used.

The overall size of the array of optical confinements can generally range from a few nanometers to a few millimeters in thickness, and from a few millimeters to 50 centimeters in width and/or length. Arrays may have an overall size of about few hundred microns to a few millimeters in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements may be placed close to each other relative to the incident wavelength.

The individual confinement in the array can provide an effective observation volume less than about 1000 zeptoliters, less than about 900, less than about 200, less than about 80, less than about 10 zeptoliters. Where desired, an effective observation volume less than 1 zeptoliter can be provided. In a preferred aspect, the individual confinement yields an effective observation volume that permits resolution of individual molecules, such as enzymes, present at or near a physiologically relevant concentration. The physiologically relevant concentrations for many biochemical reactions range from micro-molar to millimolar because most of the enzymes have their Michaelis constants in these ranges. Accordingly, preferred array of optical confinements has an effective observation volume for detecting individual molecules present at a concentration higher than about 1 micromolar ($\mu$M), or more preferably higher than 50 $\mu$M, or even higher than 100 $\mu$M.

As zero-mode-waveguide can provide an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such guide provides an extremely small observation volume effective to detect single-molecules, even when they are present at a concentration as high as in the micromolar range.

The zero-mode-waveguide of the present invention typically comprises a cladding surrounding a core (i.e., partially or fully), wherein the cladding is configured to preclude propagation of electromagnetic energy of a wavelength higher than the cutoff wavelength longitudinally through the core of the zero-mode waveguide. The cladding is typically made of materials that prevent any significant penetration of the electric and the magnetic fields of an electromagnetic radiation that is opaque and/or reflective materials. Suitable materials for fabricating the cladding include but are not limited to metals, metal oxides, alloys, and semi-conducting materials, and any combination thereof.

The internal cavity (i.e., the core) surrounded by the cladding may adopt a convenient size, shape or volume so long as propagating modes of electromagnetic radiation in the guide is effectively prevented. The core typically has a lateral dimension less than the cutoff wavelength ($\lambda c$). For a circular guide of diameter d and having a clad of perfect conductor, $\lambda c$ is approximately 1.7 times d. The cross sectional area of the core may be circular, elliptical, oval, conical, rectangular, triangular, polyhedral, or in any other shape. Although uniform cross sectional area is generally preferred, the cross sectional area may vary at any given depth of the guide if desired.

The optical performance of the ZMW can be enhanced by incorporation within a micromirror structure on the substrate. The incorporation of micromirrors and other methods of improving optical performance in multiplex systems are describe in copending U.S. patent application Ser. No. 12/567,526, filed Sep. 25, 2009, now U.S. Pat. No. 8,247,216, which is incorporated herein by reference in its entirety for all purposes.

In the context of chemical or biochemical analyses within ZMWs as well as other optical confinements, it is generally desirable to ensure that the reactions of interest are taking place within the optically interrogated portions of the confinement, at a minimum, and preferably such that only the reactions of a single molecule is occurring within an interrogated portion of an individual confinement. A number of methods may generally be used to provide individual molecules within the observation volume. A variety of these are described in co-pending U.S. patent application Ser. No. 11/240,662, filed Sep. 30, 2005, incorporated herein by reference in its entirety for all purposes, which describes, inter alia, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these.

Base Calling and Sequence Determination

The systems and methods of the inventions can result in improved sequence determination and improved base calling by monitoring the signal from nucleotide analogs labeled on their 3' hydroxyl groups, and in some cases monitoring both the signal from the 3' hydroxyl leaving group and polyphosphate label.

Further base-calling and sequence-determination methods for use in the invention are described in U.S. Pat. Nos. 8,182, 993, 8,703,422, and 8,370,079; and U.S. Patent Publication Nos. 2012/0330566 and 2013/0138358; and U.S. patent application Ser. No. 13/941,442 (filed Jul. 12, 2013), 61/993, 420 (filed May 15, 2014), and 62/028,741 (filed Jul. 24, 2014), all of which are incorporated herein by reference in their entireties for all purposes.

It is to be understood that the above description is intended to be illustrative and not restrictive. It readily should be apparent to one skilled in the art that various embodiments and -modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

What is claimed is:

1. A method for delaying the sequencing of a sequence of interest in a single-molecule, real-time sequencing reaction comprising:
simultaneously initiating a plurality of single-molecule, real-time sequencing reactions on a plurality of polymerase-template complexes, wherein each of the polymerase-template complexes comprises a polymerase enzyme and a nucleic acid template wherein the nucleic acid template comprises, in order, a priming region, a runway region, and an insert region comprising a sequence of interest, said runway region and said insert region each being from a different source, wherein from the time the polymerase incorporates its first nucleotide to the time when the polymerase enzyme sequences a first base of the insert region is greater than about 30 seconds for a majority of the polymerase-template complexes, wherein the runway region has a length based on the polymerization rate of the polymerase enzyme to provide for said about 30 seconds.

2. The method of claim 1 wherein each priming region in each nucleic acid template in each of the polymerase-template complexes comprises an identical sequence.

3. The method of claim 1 wherein each runway region in each nucleic acid template in each of the polymerase-template complexes comprises an identical sequence.

4. The method of claim 1 wherein the template nucleic acid comprises a double-stranded region and a hairpin connecting the strands of the double-stranded region.

5. The method of claim 1 wherein the template nucleic acid comprises a double-stranded region and hairpins on each end of the double-stranded region connecting the two strands.

6. The method of claim 1 wherein the single-molecule, real-time sequencing reactions comprise incorporation of nucleotide residues, wherein the incorporation of nucleotide residues is detected using fluorescence.

7. The method of claim 1 wherein the single-molecule, real-time sequencing reactions comprise incorporation of nucleotide residues, wherein the incorporation of nucleotide residues is detected electronically or magnetically.

8. The method of claim 1 wherein the single-molecule, real-time sequencing reactions comprise incorporation of nucleotide residues, wherein the incorporation of nucleotide residues is detected by electrochemistry, capacitance, conductivity, impedance, or with a field effect transducer.

9. The method of claim 1 wherein the length of the runway region is 200 nucleotides or greater.

10. The method of claim 1 wherein the length of the runway region is between 200 and 2,000 nucleotides.

11. The method of claim 1 wherein the time from the initiation of the sequencing reactions to the time of sequencing the insert region is greater than about 60 seconds for a majority of the polymerase-template complexes.

12. The method of claim 1 further comprising a barcode region between the runway region and the insert region.

13. The method of claim 1, wherein the single-molecule, real-time sequencing reaction comprises observing labels corresponding to labeled nucleotides during polymerase mediated nucleic acid synthesis.

14. The method of claim 1, wherein the single-molecule, real-time sequencing reaction comprises nanopore sequencing.

15. The method of claim 1, wherein the runway region comprises at least one modified base that is absent from the insert region.

16. A method for delaying the sequencing of a sequence of interest in a single-molecule, real-time sequencing reaction comprising:
initiating a single-molecule, real-time sequencing reaction on a polymerase-template complex, wherein the polymerase-template comprises a polymerase enzyme and a nucleic acid template, wherein the nucleic acid template comprises, in order, a priming region, a runway region, and an insert region comprising a sequence of interest, said runway region and said insert region each being from a different source, wherein from the time the polymerase incorporates its first nucleotide to the time when the polymerase enzyme sequences a first base of the insert region is greater than about 30 seconds, wherein the runway region has a length based on the polymerization rate of the polymerase enzyme to provide for said about 30 seconds.

17. The method of claim 16 wherein the template nucleic acid comprises a double-stranded region, and a hairpin connecting the strands of the double-stranded region.

18. The method of claim 16 wherein the template nucleic acid comprises a double-stranded region and hairpins on each end of the double-stranded region connecting the two strands.

19. The method of claim 16 wherein the single-molecule, real-time sequencing reactions comprise incorporation of nucleotide residues, wherein the incorporation of nucleotide residues is detected using fluorescence.

20. The method of claim 16 wherein the single-molecule, real-time sequencing reactions comprise incorporation of nucleotide residues, wherein the incorporation of nucleotide residues is detected electronically or magnetically.

21. The method of claim 16 wherein the single-molecule, real-time sequencing reactions comprise incorporation of nucleotide residues, wherein the incorporation of nucleotide residues is detected by electrochemistry, capacitance, conductivity, impedance, or with a field effect transducer.

22. The method of claim 16 wherein the length of the runway region is 200 nucleotides or greater.

23. The method of claim 16 wherein the length of the runway region is between 200 and 2,000 nucleotides.

24. The method of claim 16 wherein the runway region comprises at least one modified base that is absent from the insert region.

25. The method of claim 16 wherein the time from the initiation of the sequencing reactions to the time of sequencing the insert region is greater than about 60 seconds.

26. The method of claim 16 further comprising a barcode region between the runway region and the insert region.

* * * * *